United States Patent
Schittmayer-Schantl et al.

(10) Patent No.: US 12,216,125 B2
(45) Date of Patent: Feb. 4, 2025

(54) METHOD AND KIT FOR ISOTOPE-LABELLING OF A GLUTATHIONE-CONTAINING BIOLOGICAL SAMPLE FOR MASS SPECTROMETRY

(71) Applicant: TECHNISCHE UNIVERSITÄT WIEN, Vienna (AT)

(72) Inventors: Matthias Schittmayer-Schantl, Vienna (AT); Ruth Birner-Grünberger, Vienna (AT); Tamara Tomin, Vienna (AT)

(73) Assignee: TECHNISCHE UNIVERSITÄT WIEN, Vienna (AT)

( * ) Notice: Subject to any disclaimer, the term of this patent is extended or adjusted under 35 U.S.C. 154(b) by 1011 days.

(21) Appl. No.: 17/270,813

(22) PCT Filed: Aug. 28, 2019

(86) PCT No.: PCT/EP2019/072916
§ 371 (c)(1),
(2) Date: Feb. 23, 2021

(87) PCT Pub. No.: WO2020/043756
PCT Pub. Date: Mar. 5, 2020

(65) Prior Publication Data
US 2021/0190793 A1    Jun. 24, 2021

(30) Foreign Application Priority Data
Aug. 28, 2018 (EP) .................................. 18191196

(51) Int. Cl.
*G01N 33/68* (2006.01)
(52) U.S. Cl.
CPC ..... *G01N 33/6848* (2013.01); *G01N 33/6815* (2013.01)

(58) Field of Classification Search
CPC ................ G01N 33/6848; G01N 33/6815
See application file for complete search history.

(56) References Cited

U.S. PATENT DOCUMENTS 10,705,093 B2 * 7/2020 Fu ...................... A61K 9/0019

FOREIGN PATENT DOCUMENTS

WO    2016/015060 A1    1/2016

OTHER PUBLICATIONS

Supplementary European Search Report received in European Patent Application No. 18191196.7 dated Jan. 256, 2019.
(Continued)

*Primary Examiner* — Shafiqul Haq
(74) *Attorney, Agent, or Firm* — Greer, Burns & Crain, Ltd

(57) ABSTRACT

A method of stabilising a biological sample including glutathione (GSH) and glutathione disulfide (GSSG), including a) providing the biological sample having GSH and GSSG; b) contacting GSH and GSSG of the sample with a maleimide to obtain maleimide-alkylated GSH; c) separating excess maleimide from maleimide-alkylated GSH and GSSG; d) contacting maleimide-alkylated GSH and GSSG with a reducing agent such as TCEP under conditions which allow reduction of GSSG by the reducing agent such as TCEP to obtain further GSH; and e) contacting maleimide-alkylated GSH and GSH with a heavy isotopologue of the maleimide to obtain a heavy isotopologue of the maleimide-alkylated GSH. A stabilised biological sample is provide containing maleimide-alkylated GSH and a heavy isotopologue thereof, as well as a mass-spectrometric method for quantifying maleimide-alkylated GSH and a heavy isotopologue thereof in a sample and a kit for stabilising a biological sample including GSH and GSSG for mass spectrometric analysis.

6 Claims, 8 Drawing Sheets

(56) References Cited

OTHER PUBLICATIONS

International Search Report and Written Opinion received for PCT/EP2019/072916 mailed Oct. 21, 2019.
Apuy, J., et al., "Ratiometric Pulsed Alkylation/Mass Spectrometry of the Cysteine Pairs in Individual Zinc Fingers of MRE-Binding Transcription Factor-1 (MTF-1) as a Probe of Zinc Chelate Stability," Biochemistry, 2001, 40, pp. 15164-15175.
Danielson, S., et al., "Quantitative Mapping of Reversible Mitochondrial Complex I Cysteine Oxidation in a Parkinson Disease Mouse Model," Journal of Biological Chemistry, 2011, vol. 286, No. 9, pp. 7601-7608.
Deponte, M., "Glutathione catalysis and the reaction mechanisms of glutathione-dependent enzymes," Biochimica et Biophysica Acta 1830, 2013, pp. 3217-3266.
Forman, J., et al., "Glutathione: Overview of its protective roles, measurement, and biosynthesis," Mol Aspects Med. 2009, vol. 30(1-2): 12 pages.
Giustarini, D., et al., "Analysis of GSH and GSSG after derivatization with N-ethylmaleimide," Nature Protocols, 2013, vol. 8, No. 9, pp. 1660-1669.
Giustarini, D., et al., "Pitfalls in the analysis of the physiological antioxidant glutathione (GSH) and its disulfide (GSSG) in biological samples: An elephant in the room," Journal of Chromatography B, 2016, pp. 21-28.
Griffith, O., "Determination of Glutathione adn Glutathione Disulfide Using Glutathione Reductase and 2-Vinylpyridine," Analytical Biochemistry 106, 1980, pp. 207-212.
Jubiz, W., et al., "N-Ethylmaleimide Prevents Destruction of Corticotropin (ACTH) in Plasma," Clin. CHem 24/5, 1978, pp. 826-827.
Keith, M., et al., "Increased Oxidative Stress in Patients With Congestive Heart Failure," JACC vol. 31, No. 6 May 1998, pp. 1352-1356.
Leonard, S., et al., "Chemical 'omics' approaches for understanding protein cysteine oxidation in biology," Current Opinion in Chemical Biology 15, 2011, pp. 88-102.
Lu, S., "Glutathione Synthesis," Biochim Biophys Acta., 1830(5), May 2013, pp. 3143-3153.
McDonagh, B., et al., "Differential Cysteine Labeling and Global Label-Free Proteomics Reveals an Altered Metabolic State in Skeletal Muscle Aging," ACS Journal of Proteome Research, 2014, 14 pages.
Moore, T., et al., "A new LC-MS/MS method for the clinical determination of reduced and oxidized glutathione from whole blood," J. Chromatogr. B 929, 2013, pp. 51-55.
Mehra, S., "Stability of eosin-5'-maleimide dye used in flow cytometric analysis for red cell membrane disorders," Blood Research, vol. 50, No. 2, Jun. 2015, pp. 109-112.
Rajer, M., et al., "Quantitative analysis of fine needle aspiration biopsy samples," Radiol Oncol, 39(4), 2005, pp. 269-272.
Reinbold, J., et al., "Quantitation of glutathione and its oxidation products in erythrocytes by multiple-label stable-isotope dilution," Analytical Biochemistry 445, 2014, pp. 41-48.
Sentellas, S., et al., "GSSG/GSH ratios in cryopreserved rat and human hepatocytes as a biomarker for drug induced oxidative stress," Toxicology in Vitro 28, 2014, pp. 1006-1015.
Sinha, V., et al., "Proteomic and mass spectroscopic quantitation of protein Snitrosation differentiates NO-donors," ACS Chem Biol., 5(7), Jul. 16, 2010, pp. 667-680.
Sutton, T., et al., "A robust and versatile mass spectrometry platform for comprehensive assessment of the thiol redox metabolome," Redox Biology 16, 2018, pp. 359-380.
Svardal, A., et al., "Determination of Reduced, Oxidized, and Protein-Bound Glutathione in Human Plasma with Precolumn Derivitization with Monobromobimane and Liquid Chromatography," Analytical Biochemistry 184, 1990, pp. 338-346.
Tietze, F., "Enzymic Method for Quantitative Determination of Nanogram Amounts of Total and Oxidized Glutathione: Applications to Mammalian Blood and Other Tissues," Analytical Biochemistry 27, 1969, pp. 502-522.
Townsend, D., et al., "The importance of glutathione in human disease," Biomed Pharmacother., 57(3-4), 2003, pp. 145-155.
Zitka, O., et al., "Redox status expressed as GSH:GSSG ratio as a marker for oxidative stress in paediatric tumour patients," Oncology Letters 4, 2012, pp. 1247-1253.

\* cited by examiner

METHOD AND KIT FOR ISOTOPE-LABELLING OF A GLUTATHIONE-CONTAINING BIOLOGICAL SAMPLE FOR MASS SPECTROMETRY

BACKGROUND

The field of present invention relates to methods of stabilising and isotope-labelling a biological sample comprising glutathione (GSH) and glutathione disulfide (GSSG), in particular for subsequent mass spectrometric analysis, as well as kits for this purpose.

GSH (also known as γ-L-glutamyl-L-cysteinyl-glycine) is the main endogenous, thiol-based antioxidant in organisms. GSH can be oxidized to GSSG which in turn can be reduced back to GSH. Typically, more than 98% of the total glutathione pool in the cell consists of GSH in the concentration range of 1-10 mmol/L while GSSG accounts for the residual 1-2% (Forman et al.). GSH can act as nucleophile adaptor for various different electrophiles (Deponte). However, its predominant role is the removal of hydrogen peroxides by acting as a cofactor for the selenium-based enzyme family glutathione peroxidase (GPx), see Lu. As a result, two GSH molecules donate a pair of electrons reducing hydrogen peroxide to water while being in turn oxidized to GSSG (Giustarini et al.). Glutathione reductase (GR) recycles GSSG to GSH in an NADPH dependent manner. However more extensive oxidative stress can alter the GSH to GSSG ratio, either because of insufficient capacity of GR or redox imbalance (Townsend et al.). Therefore, GSH to GSSG ratio can be used as a readout of tissue redox state (Zitka et al.).

Disturbed GSH homeostasis has been reported in various different pathological conditions, most prominently in cancer, diabetes, neurodegenerative and cardiovascular diseases. In heart related conditions, oxidative stress is correlated to heart failure and development of coronary diseases. It has been proposed that GSH/GSSG ratio can act as an independent prognostic marker for atherosclerosis and risk of death in patients with coronary disease.

Due to the importance of GSH homeostasis in health and disease, several assays for quantitating GSH and/or GSSG in biological samples have been established in the prior art. As the cellular GSH concentration is usually approximately 2 orders of magnitude higher than the GSSG concentration, it was found that post sampling oxidation of even a small fraction of GSH to GSSG could lead to a severe bias of the concentration measured for the latter. Therefore, in order to prevent artificially high GSSG levels, biological samples to be analysed for their GSH/GSSG ratio are typically treated with a thiol-quenching reagent, which blocks free GSH immediately after sampling and prior to further sample processing.

Traditional colorimetric assays for determination of GSH in biological samples are based on reaction of the free thiol group with Ellman's reagent (5,5'-dithiobis-2-nitrobenzoic acid, DTNB) or a similar dye. A drawback of this approach is that Ellman's reagent will react with any soluble thiol and other small polar thiol containing molecules, e.g. cysteine, which will add to the observed signal.

For detection of GSSG, GSSG may be reduced either chemically or enzymatically. In the latter approach, the substrate specificity of the enzyme also confers assay selectivity. An assay allowing detection of GSSG by first blocking free GSH with N-ethyl-maleimide (NEM) and subsequent enzymatic reduction of GSSG and detection with Ellman's reagent was disclosed (see Tietze). A drawback of this assay is the laborious removal of NEM after the initial blocking step, as NEM inhibits the NADPH dependent enzyme GR employed in this enzyme coupled assay. This drawback was partly addressed by using 2-vinylpyridine to block GSH instead of NEM (Griffith). However, using 2-vinylpyridine has other disadvantages such as slower reaction kinetics and limited membrane permeability as well as interfering with the colorimetric reaction, leading at least to lower sensitivity of the Griffith assay.

Svardal et al. relate to the determination of reduced, oxidized, and protein-bound glutathione in human plasma with precolumn derivatisation with monobromobimane and liquid chromatography. Essentially, the assay disclosed therein is based on liquid chromatography and fluorescence detection.

Jubiz & Nolan relate to NEM preventing destruction of corticotropin (ACTH) in plasma. While the document discloses use of NEM with blood samples in general, the document is completely silent on GSH/GSSG determination. The latter also applies to Mehra et al. This document merely relates to the stability of a maleimide dye used in flow cytometric analysis for red cell membrane disorders. The maleimide dye is disclosed to be added to washed donor red blood cells in a flow tube, i.e. not in a blood collection tube.

Apuy et al. relates to ratiometric pulsed alkylation/mass spectrometry of the cysteine pairs in individual zinc fingers of MRE-binding transcription factor-1 (MTF-1) as a probe of zinc chelate stability. In the section "ratio-metric pulsed alkylation/mass spectrometry", d5-NEM and NEM are disclosed to be subsequently added to a sample comprising the protein MTF-1. The document is silent on GSH and GSSG as well as on blood collection in general and blood collection tubes in particular.

With the rise of liquid chromatography coupled mass spectrometry (LC-MS), the requirement of enzyme coupling for selective GSSG detection has diminished. However, the need to protect free GSH from oxidation remains. Numerous agents for blocking free GSH are employed in the field, such as iodoacetic acid, NEM, phtalimide and dithionitrobenzoate. In other words, the field has not yet settled on a single GSH blocking agent and advantages and disadvantages of various blocking agents remain a subject of discussion.

Sample preparation methods for GSH- and GSSG-containing biological samples with subsequent LC-MS measurement are disclosed e.g. by Reinbold et al., Moore et al., Sutton et al. and Sentellas et al. WO 2016/015060 A1 also discloses an MS-based method for determining the level of thiol and disulphide containing molecules in a sample, among them GSH or GSSG. However, all of these methods have drawbacks such as being comparatively complex, requiring several expensive reagents and/or leading to comparatively low measurement sensitivity.

It is thus an object of the present invention to provide improved methods and tools for the preparation of GSH- and GSSG-containing biological samples, in particular to increase the accuracy and/or sensitivity of an LC-MS measurement of GSH and GSSG following the sample preparation.

SUMMARY

The present invention provides a method of stabilising a biological sample comprising glutathione (GSH) and glutathione disulfide (GSSG), the method comprising the following steps:

a) providing the biological sample comprising GSH and GSSG, b) contacting GSH and GSSG of the biological sample with a maleimide under conditions which allow alkylation of the sulfhydryl group of GSH with the maleimide to obtain maleimide-alkylated GSH, c) separating excess maleimide from maleimide-alkylated GSH and GSSG, d) contacting maleimide-alkylated GSH and GSSG with a reducing agent, selected from the group consisting of phosphine-based reducing agents such as tris(2-carboxyethyl)phosphine (TCEP) or tributylphosphine, and thiol-based reducing agents such as dithiothreitol (DTT), dithioerythritol (DTE) or β-mercaptoethanol, under conditions which allow reduction of GSSG by the reducing agent to obtain further GSH, and e) contacting maleimide-alkylated GSH and GSH with a heavy isotopologue of the maleimide under conditions which allow alkylation of the sulfhydryl group of GSH with the heavy isotopologue of the maleimide to obtain a heavy isotopologue of the maleimide-alkylated GSH.

The present invention also provides a stabilised biological sample containing maleimide-alkylated GSH and a heavy isotopologue thereof, obtainable by the inventive method. Herein, the term "stabilised" shall mean that the sample is at least stabilised with respect to the GSH/GSSG redox couple, i.e. that GSH and GSSG are stabilised by alkylation such that essentially no interconversion between the two occurs any more.

In another aspect, the present invention provides a biological sample or standard for mass spectrometry containing a below 4000 Da, even more preferably below 3000 Da, yet even more preferably below 2000 Da, especially below 1500 Da or even below 1000 Da.

In yet another aspect, the present invention provides a method for quantifying maleimide-alkylated GSH and a heavy isotopologue thereof in a biological sample, the method comprising the following steps:

providing the biological sample of the present invention, optionally, purifying the biological sample in a liquid chromatography system, and analysing at least a fraction of the biological sample, which fraction contains at least a portion of the maleimide-alkylated GSH and the heavy isotopologue thereof, in a mass spectrometer to measure the abundance of the maleimide-alkylated GSH and the heavy isotopologue thereof.

In yet another aspect, the present invention provides a kit for stabilising a biological sample comprising GSH and GSSG for mass spectrometric analysis, the kit comprising a first container containing a maleimide, a second container containing a heavy isotopologue of the maleimide, and preferably a heavy isotopologue of a maleimide-alkylated

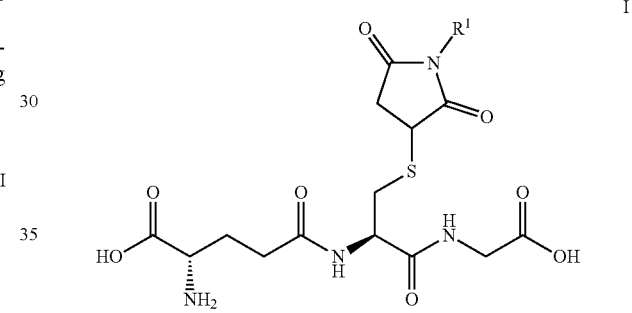

GSH of formula I wherein $R^1$ is selected from the group consisting of methyl, ethyl, propyl, butyl, pentyl, and PEGs, in particular PEGs with a molecular mass below 5000 Da, preferably below 4000 Da, even more preferably below 3000 Da, yet even more preferably below 2000 Da, especially below 1500 Da or even below 1000 Da; preferably in the first container or in a third container. Preferably, the kit comprises a fourth container containing a reducing agent, selected from the group consisting of phosphine-based reducing agents such as TCEP or tributylphosphine, and thio-based reducing agents such as DTT, DTE or β-mercaptoethanol.

In even yet another aspect, the present invention provides a blood collection tube containing (being pre-filled with) a maleimide, preferably in its solid form (i.e. not dissolved, e.g. present as a powder). Most typically, the blood collection tube is sterile.

In the course of the present invention, it was surprisingly found that with the inventive sample preparation approach sensitivity of subsequent mass-spectrometric GSSG determination was strongly increased. In fact, the sensitivity was improved by a factor of 10 compared to direct measurement of GSSG (see example 5 and in particular Table 2), which was entirely unexpected.

Beyond that, the greatly simplified sample handling achieved by methods and kits of the present invention is especially beneficial in a clinical setting, where strictly time-controlled sample preparation is often infeasible.

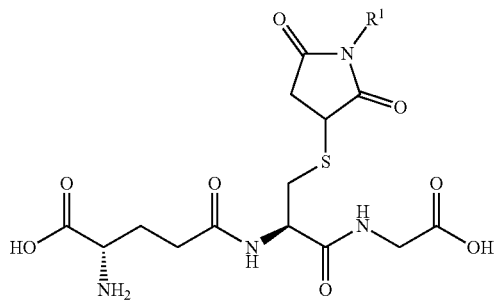

maleimide-alkylated GSH of formula I
and a maleimide-alkylated GSH of formula II

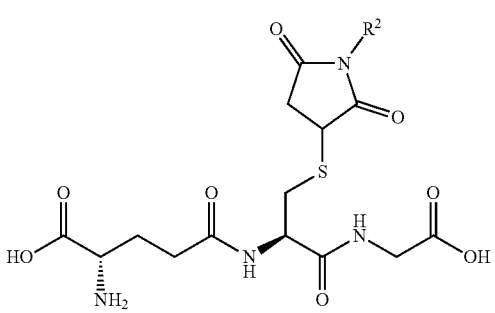

wherein $R^2$ is a heavy isotopologue of $R^1$, wherein $R^1$ is selected from the group consisting of methyl, ethyl, propyl, butyl, pentyl, and poly-ethylene glycols (PEGs), in particular PEGs with a molecular mass below 5000 Da, preferably The detailed description given below relates to all of the above aspects of the invention unless explicitly excluded.

Using a sensitive and reliable method for clinical assessment of GSH/GSSG status has a particular relevance since the redox couple can be used as a biomarker for oxidative stress. Oxidative stress plays a significant role in development and progression of various pathologies, in particular cardiovascular diseases, where it is reported to be closely correlated with the risk of heart failure (see Keith et al.). This is of special importance considering a growing need for development in the field of heart failure prognostics. Currently, one in eight deaths is due to heart failure with a predicted increase in mortality rate by 46% over the next 12 years. One of the major physiological conditions leading to failing heart is cardiomyopathy (especially dilated cardiomyopathy) and it has already been correlated to oxidative stress and disturbed GSH homeostasis. Using the inventive method, it was confirmed that GSH/GSSG ratio is decreased in heart tissues of patients with heart failure (see e.g. FIG. 8), which serves as scientific validation of the inventive method.

Evidently, high sensitivity is vital when the sample is scarce. Typical scarce samples for which sensitivity plays an important role are biopsies. Commonly, several different tests have to be carried out on a single biopsy and therefore only a small fraction of tissue is available for each of them. GSH/GSSG mass-spectrometric assays can be performed with much smaller sample amounts than for instance redox proteomics assays (as disclosed e.g. in Sinha et al., McDonagh et al. or Leonard et al.). In view of its exceptional sensitivity, the inventive method is especially suitable to test biopsies, in particular biopsies obtained by minimally invasive techniques such as fine needle aspiration which usually only comprise about 500,000 cells (as disclosed in Rajer et al.).

Taken together, the isotopologue-based design of the inventive method compensates for different matrix effects as analytes co-elute from liquid chromatography and can be ionized in parallel. As mentioned, another major advantage of the method is the large improvement of sensitivity. Measuring GSSG in form of GSH-d5-NEM boosted the sensitivity of the method at least 10-fold. Therefore, minimum sample amounts are required, rendering the method compatible with minimally invasive clinical sampling procedures. The method presented herein therefore represents a sensitive, cost-effective and simple alternative for accurate determination of the GSH/GSSG ratio, the major redox readout of mammalian systems.

As used herein, "conditions which allow alkylation of the sulfhydryl group of GSH with the maleimide" typically require that the maleimide (such as NEM) is (initially) present at a concentration of at least 0.0001 mM, preferably at least 0.001 mM, more preferably at least 0.01 mM, even more preferably at least 0.1 mM, yet even more preferably at least 1 mM or even at least 2 mM. Typically, such conditions comprise a pH between 6 and 8, preferably between 6.25 and 7.75, in particular between 6.5 and 7.5, and/or incubation temperatures from 5° C. to 45° C., preferably from 10° C. to 40° C., more preferably from 15° C. to 35° C., especially from 20° C. to 30° C. Incubation times may range for instance between 5 and 60 minutes.

As used herein, "conditions which allow alkylation of the sulfhydryl group of GSH with the heavy isotopologue of the maleimide" typically require that the heavy isotopologue of the maleimide (such as d5-NEM) is (initially) present at a concentration of at least 0.001 mM, preferably at least 0.01 mM, more preferably at least 0.1 mM, even more preferably at least 1 mM, yet even more preferably at least 10 mM or even at least 50 mM. Typically, such conditions comprise a pH between 6 and 8, preferably between 6.25 and 7.75, in particular between 6.5 and 7.5, and/or incubation temperatures from 5° C. to 45° C., preferably from 10° C. to 40° C., more preferably from 15° C. to 35° C., especially from 20° C. to 30° C. Incubation times may range for instance between 5 and 60 minutes. Most typically, the heavy isotopologue of the maleimide is added in excess to the reducing agent (such as TCEP) previously added.

As used herein, "conditions which allow reduction of GSSG by the reducing agent" typically require that the reducing agent (such as TCEP) is (initially) present at a concentration of at least 0.001 mM, preferably at least 0.01 mM, more preferably at least 0.1 mM, even more preferably at least 1 mM, yet even more preferably at least 10 mM or even at least 25 mM. Typically, such conditions comprise a pH between 6 and 8, preferably between 6.25 and 7.75, in particular between 6.5 and 7.5, and/or incubation temperatures from 5° C. to 45° C., preferably from 10° C. to 40° C., more preferably from 15° C. to 35° C., especially from 20° C. to 30° C. Incubation times may range for instance between 5 and 60 minutes. Typically, the reducing agent (such as TCEP) is added in excess to residual maleimide (for instance, a small amount of residual maleimide may have remained after solvent extraction, e.g. with dichloromethane).

As used herein, the term "biological sample" refers to any sample obtained from a biological source (e.g. a living organism such as a mammal), said obtaining optionally comprising processing steps such as drying, freezing, homogenising or fractionating. It is however preferred to avoid such processing steps as much as possible in order to increase accuracy of the subsequent measurement. Typically, the biological sample further comprises at least one compound (preferably at least two, more preferably all) selected from cysteine alkylated with the maleimide (such as NEM) or the heavy isotopologue thereof, glycine-cysteine dipeptide alkylated with the maleimide (such as NEM) or the heavy isotopologue thereof and insulin alkylated with the maleimide (such as NEM) or the heavy isotopologue thereof.

Specifically, within the context of the present invention, the biological sample is preferably obtained from an individual, preferably a mammal, in particular a human (e.g. through biopsy or phlebotomy, in particular if collected into an (previously evacuated) blood collection tube as defined herein). In particular, the individual has or is suspected of having a disease or condition, in particular selected from the group of cancers, metabolic conditions or diseases, such as diabetes, cardiovascular diseases or conditions, such as heart failure, and neurodegenerative diseases.

The biological sample may be a blood sample (such as a serum sample, a plasma sample or a whole-blood sample) or a tissue sample, preferably a biopsy sample, in particular a needle aspiration biopsy sample (needle aspiration biopsy is also called fine needle aspiration biopsy herein). In order to work as closely to the physiological state of the GSH/GSSG redox pair as possible, it is preferred that the biological sample comprises cells (such as mammalian or human cells) which comprise GSH and GSSG.

In the context of the present invention, the biological sample may be provided in a blood collection tube.

According to a further preferred embodiment, the inventive method further comprises the step of lysing the cells. Preferably, such lysis is performed concomitantly by the solvent precipitation of protein disclosed herein, in particular wherein the solvent is ethanol, methanol, acetonitrile or a mixture thereof.

According to a preferred embodiment, the inventive method further comprises the step of adding a buffer solution to the biological sample before said contacting step b). Preferably, the buffer solution already contains the maleimide, in particular at a concentration of at least 0.0001 mM, preferably at least 0.001 mM, more preferably at least 0.01 mM, even more preferably at least 0.1 mM, yet even more preferably at least 1 mM or even at least 2 mM (and preferably not more than 50 mM or not more than 25 mM or not more than 10 mM). It is especially preferred that the buffer solution has a pH between 6 and 8, preferably between 6.25 and 7.75, in particular between 6.5 and 7.5. By way of example, phosphate-buffered saline (PBS) may be used as buffer solution.

It is particularly preferred when the buffer solution is added directly to the cells (i.e. when they are still intact), especially when it contains the maleimide. This increases the accuracy of a subsequent MS measurement. Preferably, before said adding step, the cells are concentrated (e.g. by centrifugation) and/or at least a portion of the liquid fraction (e.g. cell medium) of a suspension the cells are in is removed.

Further, in case the biological sample is a blood sample such as a serum sample, a plasma sample or a whole-blood sample, or a tissue sample, preferably a biopsy sample, in particular a needle aspiration biopsy sample, it is particularly preferred as well when the buffer solution (especially when it contains the maleimide) is added directly to the biological sample.

In the course of the present invention it was found that avoiding a delay in adding the maleimide to a blood sample (i.e. adding the maleimide to the blood sample directly after blood collection) reduces error in GSH/GSSG-ratio measurements (see FIG. 7 and Example 7). Consequently, in a further, especially preferred embodiment of the present invention, step b) occurs in a blood collection tube pre-filled with the maleimide, in order to allow for immediate alkylation of GSH in the blood sample (when the blood is freshly drawn from the patient).

Blood collection tubes in general are well known and widely-used in clinical practice. Blood collection tubes may be evacuated (prior to blood collection; to allow drawing of a pre-defined volume of blood) or operated by aspiration (i.e. with a plunger). Typically, these tubes have a volume from 5-15 ml for drawing 2-10 ml of blood ("draw volume"). Blood collection tubes are for instance commercially available from Becton, Dickinson and Company)(VACUTAINER®), Greiner Bio-One (VACUETTE®), Sarstedt) (S-MONOVETTE®) and Terumo (VENOSAFE®). They may be pre-filled with coagulants, anticoagulants and/or other reagents which react immediately with freshly drawn blood. Within the context of the present invention, the blood collection tube may be an evacuated blood collection tube or a blood collection tube operated by aspiration. In particular, the blood collection tube may be a serum separator tube.

In the context of the present invention (in particular the kit aspect and the blood collection tube aspect), the blood collection tube is most typically sterile.

In the context of the present invention, the blood collection tube preferably contains (is pre-filled with) at least 0.01 µmol of the maleimide (e.g. NEM), preferably at least 0.1 µmol of the maleimide, more preferably at least 1 µmol of the maleimide, especially at least 2.5 µmol or even at least 5 µmol of the maleimide. Typically, the blood collection tube does not contain more than 500 µmol of the maleimide, preferably does not contain more than 250 µmol of the maleimide, more preferably does not contain more than 100 µmol of the maleimide, especially not more than 50 µmol of the maleimide.

It is highly preferred that the maleimide (such as NEM) is present in the blood collection tube in its solid form (i.e. not dissolved; e.g. present as a powder).

According to a preferred embodiment, the blood collection tube further comprises an anticoagulant preferably selected form the group consisting of heparin, ethylenediaminetetraacetate (EDTA), citrate and fluoride, preferably heparin or EDTA, or further comprises a coagulant preferably micronized silica particles or thrombin.

It was found that using another heavy isotopologue of the maleimide-alkylated GSH (i.e. not the one obtained in step e) of the method) as an internal standard increases the quality of the measurement. Accordingly, in a further preferred embodiment, the blood collection tube is further pre-filled with (preferably a pre-set molar amount of) another heavy isotopologue of the maleimide-alkylated GSH, such as $^{13}C_2$, $^{15}N$-GSH-d5-NEM. Independently of the nature of the biological sample (i.e. also in case it is not a blood sample), such internal standard may be added according to the method, e.g. before step b), or between step b) and step c), or after step e).

To increase the quality of a subsequent measurement by ensuring completeness of the alkylation reaction as much as possible, the inventive method further comprises, in a preferred embodiment, the step of incubating the biological sample at a temperature from 5° C. to 45° C., preferably from 10° C. to 40° C., more preferably from 15° C. to 35° C., especially from 20° C. to 30° C. for a period of time during said contacting step b) and/or e). In addition, or alternatively thereto, the biological sample may be incubated at a pH between 6 and 8, preferably between 6.25 and 7.75, in particular between 6.5 and 7.5, for a period of time during said contacting step b) and/or e). Said period of time may e.g. be between 0.01 and 24 hours, for instance between 1 and 60 minutes.

In the course of the present invention, it was found that solvent extraction is suitable for removing sufficient excess maleimide from the alkylation reaction to allow downstream proceedings steps, while at the same time being faster and allowing for easier handling than methods conventionally used for removing excess maleimide in sulfhydryl labelling reactions. Therefore, in a further preferred embodiment of the inventive method, in step c), excess maleimide is separated from maleimide-alkylated GSH and GSSG by solvent extraction, preferably wherein the solvent is an (essentially water-immiscible) organic solvent, in particular selected from the group consisting of dichloromethane, chloroform, ethyl acetate, hexane, an ether such as diethyl ether, and mixtures thereof.

Furthermore, in the course of the present invention it turned out that, if the biological sample comprises protein (typical biological samples such as cell samples or biopsy samples do, of course), it is beneficial to remove the protein from species to be measured by MS for increased accuracy and sample stability as well as reduced loss of (typically very expensive) heavy isotopologue of maleimide in the labelling reaction (which would be partially quenched by sulfhydryl groups present in protein). Thus, in a further preferred embodiment of the present invention, the method further comprises separating protein from maleimide-alkylated GSH and GSSG. Preferably, this comprises solvent precipitation of protein, in particular wherein the solvent is ethanol, methanol, acetonitrile or a mixture thereof. Preferably the separating is conducted before step c).

In the context of the present invention, the following maleimide is particularly suitable:

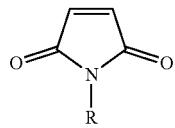

wherein R is selected from the group consisting of methyl, ethyl, propyl, butyl, pentyl, and PEGs (in particular PEGs with a molecular mass below 5000 Da, preferably below 4000 Da, even more preferably below 3000 Da, yet even more preferably below 2000 Da, especially below 1500 Da or even below 1000 Da).

According to an especially preferred embodiment, the maleimide is NEM. Preferably, the heavy isotopologue of the maleimide is d5-NEM:

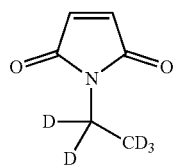

In a further preferred embodiment of the present invention, the method further comprises the step of concentrating and/or drying the sample, or a fraction thereof, comprising the maleimide-alkylated GSH and preferably the heavy isotopologue thereof, preferably between step b) and step c) or between step c) and step d) or after step e) of the method of the present invention. Any concentrating or drying method known in the art may be used, for instance vacuum centrifugation or lyophilisation.

The biological sample of the present invention is preferably dry (after the inventive stabilisation method has been applied), as this further increases stability. It is evident that the presence of a certain level of residual moisture in the biological sample of the present invention is not excluded by the expression "dry", for the presence of a detectable low level of residual moisture can typically not be avoided completely. Preferably, the residual moisture of the inventive biological sample does not exceed 10% (w/w), in particular it does not exceed 5% (w/w), or even does not exceed 1% (w/w).

Typically, the maleimide-alkylated GSH and/or the heavy isotopologue thereof is present in the biological sample (after the inventive stabilisation method has been applied) at a concentration of at least 0.0001 ppm, preferably at least 0.001 ppm, more preferably at least 0.01 ppm, even more preferably at least 0.1 ppm, in particular at least 1 ppm or even at least 10 ppm. Herein, unless specified otherwise, "ppm" is to be understood as "ppmw" (i.e. parts-per-million by weight).

For optional LC-MS analysis of the biological sample of the present invention, any suitable LC-MS known in the art may be used.

In respect to the MS step, analysis by multiple-reaction monitoring (MRM) turned out to be very suitable. Accordingly, in a preferred embodiment of the inventive method of quantifying maleimide-alkylated GSH and a heavy isotopologue thereof in a biological sample, the mass spectrometer is preferably operated in an MRM mode.

Turning to the inventive kit for stabilising a biological sample, the kit's maleimide and heavy isotopologue thereof are preferably as defined hereinabove.

In a preferred embodiment, the kit comprises a heavy isotopologue of a maleimide-alkylated GSH of formula I

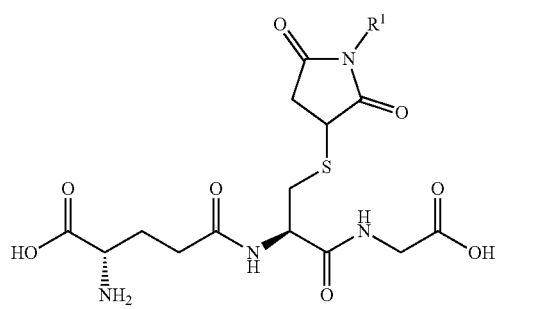

wherein $R^1$ is selected from the group consisting of methyl, ethyl, propyl, butyl, pentyl, and PEGs (in particular PEGs with a molecular mass below 5000 Da, preferably below 4000 Da, even more preferably below 3000 Da, yet even more preferably below 2000 Da, especially below 1500 Da or even below 1000 Da). This heavy isotopologue may be used as internal standard and e.g. spiked in during sampling handling. It may be present in the first container (especially if the first container is a blood collection tube, see below), in particular in a pre-set molar amount, or in a third container. This heavy isotopologue of the maleimide-alkylated GSH is preferably $^{13}C_2$, $^{15}N$-GSH-d5-NEM.

In a preferred embodiment of the present invention, the first container of the kit is a blood collection tube as defined hereinabove. Especially in this case, the kit comprises a plurality of said first container, in particular at least two, preferably at least five, even more preferably at least ten.

According to a further preference, the maleimide and/or the heavy isotopologue of the maleimide-alkylated GSH is present in its solid form in said first container, the latter preferably in a pre-set molar amount.

The kit may further comprise usage instructions, e.g. instructions to use the kit according to the inventive method. The kit may further comprise another container with a, preferably dry, biological sample of the present invention as a reference sample.

Furthermore, the kit may comprise additional containers with other components, such as a container with an organic solvent selected from the group consisting of dichloromethane, chloroform, ethyl acetate, hexane, an ether such as diethyl ether, and mixtures thereof and/or a container with ethanol, methanol, acetonitrile or a mixture thereof.

Now turning to the inventive blood collection tube aspect, blood collection tubes may be evacuated (prior to blood collection; to allow drawing of a pre-defined volume of blood) or operated by aspiration (i.e. with a plunger). Typically, these tubes have a volume from 5-15 ml for drawing 2-10 ml of blood ("draw volume"). Blood collection tubes are for instance commercially available from Becton, Dickinson and Company) (VACUTAINER®), Greiner Bio-One (VACUETTE®), Sarstedt (S-MONOVETTE®) and Terumo (VENOSAFE®). They may be pre-filled with coagulants, anticoagulants and/or other reagents which react immediately with freshly drawn blood.

Within the context of the present invention, the blood collection tube may be an evacuated blood collection tube or a blood collection tube operated by aspiration. In particular, the blood collection tube may be a serum separator tube.

Preferably, the maleimide present in the blood collection tube is the maleimide as defined hereinabove, in particular NEM.

In a preferred embodiment, the blood collection tube comprises an anticoagulant preferably selected form the group consisting of heparin, ethylenediaminetetraacetate (EDTA), citrate and fluoride, preferably heparin or EDTA, or further comprising a coagulant preferably micronized silica particles or thrombin.

Furthermore, it is preferred that the blood collection tube further comprises a heavy isotopologue of a maleimide-alkylated

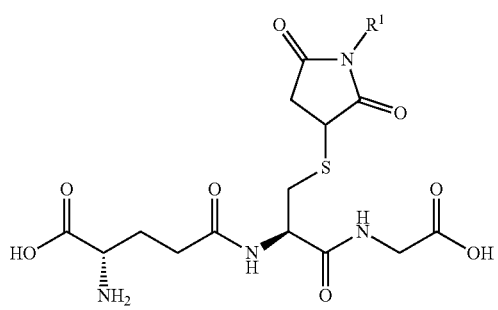

I

GSH of formula I wherein $R^1$ is selected from the group consisting of methyl, ethyl, propyl, butyl, pentyl and PEGs. The heavy isotopologue may for instance be 13C2, 15N-GSH-d5-NEM. This may be used as internal standard.

In particular, the heavy isotopologue of the maleimide-alkylated GSH is present in its solid form in the blood collection tube (i.e. not dissolved, e.g. present as a powder). In addition, or alternatively thereto, this heavy isotopologue is present in (pre-filled into) the blood collection tube in a pre-set molar amount.

In embodiments, the kit of the present invention or the blood collection tube of the present invention (in particular a plurality thereof, such as at least two or at least five) may be present in a closed, preferably sealed, package, especially wherein the kit or the blood collection tube(s) is/are sterile or sterilized.

Herein, the term "pre-set molar amount" means that the molar amount is known to a high degree of accuracy beforehand (as given e.g. in the usage instructions), preferably with an error of less than 10%, more preferably less than 5%, even more preferably less than 1%, especially less than 0.1%. This is useful for absolute quantification in LC-MS.

As used herein, the term "heavy isotopologue of compound X" (e.g. heavy isotopologue of the maleimide) shall refer to heavy stable isotopologues of compound X, i.e. isotopologues which are non-radioactive. In such isotopologues, one or more atoms forming compound X and usually present in the form of a light isotope (e.g. $^1H$, $^{12}C$ or $^{14}N$) are present in the form of a heavier isotope (e.g. D ($^2H$), $^{13}C$ or $^{15}N$) instead. It is evident that the term does not relate to a naturally-occurring mixture of isotopologues (e.g. with a relative abundance of $^{14}N$ of 99.6% and of $^{15}N$ with 0.4%).

The present invention further relates to the following embodiments:

Embodiment 1. A method of stabilising a biological sample comprising glutathione (GSH) and glutathione disulfide (GSSG), the method comprising the following steps:
  a) providing the biological sample comprising GSH and GSSG,
  b) contacting GSH and GSSG of the biological sample with a maleimide under conditions which allow alkylation of the sulfhydryl group of GSH with the maleimide to obtain maleimide-alkylated GSH,
  c) separating excess maleimide from maleimide-alkylated GSH and GSSG,
  d) contacting maleimide-alkylated GSH and GSSG with a reducing agent, selected from the group consisting of phosphine-based reducing agents such as tris(2-carboxyethyl)phosphine (TCEP) or tributylphosphine, and thiol-based reducing agents such as dithiothreitol (DTT), dithioerythritol (DTE) or β-mercaptoethanol, under conditions which allow reduction of GSSG by the reducing agent to obtain further GSH, and
  e) contacting maleimide-alkylated GSH and GSH with a heavy isotopologue of the maleimide under conditions which allow alkylation of the sulfhydryl group of GSH with the heavy isotopologue of the maleimide to obtain a heavy isotopologue of the maleimide-alkylated GSH;
  whereby a stabilised biological sample, comprising the maleimide-alkylated GSH and the heavy isotopologue thereof, is obtained.

Embodiment 2. The method of embodiment 1, wherein the biological sample is a blood sample, wherein step b) occurs in a blood collection tube pre-filled with the maleimide.

Embodiment 3. The method of embodiment 2, wherein the blood collection tube is further pre-filled with another heavy isotopologue of the maleimide-alkylated GSH for use as an internal standard, preferably in a pre-set molar amount.

Embodiment 4. The method of embodiment 2 or 3, wherein the blood collection tube further comprises an anticoagulant preferably selected form the group consisting of heparin, ethylenediaminetetraacetate (EDTA), citrate and fluoride, preferably heparin or EDTA, or further comprises a coagulant preferably micronized silica particles or thrombin.

Embodiment 5. The method of any one of embodiments 2 to 4, wherein the blood collection tube is a serum separator tube.

Embodiment 6. The method of any one of embodiments 1 to 5, wherein the reducing agent is TCEP.

Embodiment 7. The method of any one of embodiments 1 to 6, wherein, in step c), excess maleimide is separated from maleimide-alkylated GSH and GSSG by solvent extraction, preferably wherein the solvent is an organic solvent, in particular selected from the group consisting of dichloromethane, chloroform, ethyl acetate, hexane, an ether such as diethyl ether, and mixtures thereof.

Embodiment 8. The method of any one of embodiments 1 to 7, wherein the biological sample further comprises protein, the method further comprising separating protein from maleimide-alkylated GSH and GSSG, preferably comprising solvent precipitation of protein, in particular wherein the solvent is ethanol, methanol, acetonitrile or a mixture thereof; preferably wherein the separating is conducted before step c).

Embodiment 9. The method of any one of embodiments 1 to 8, wherein the maleimide is:

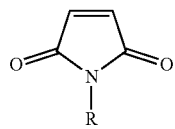

wherein R is selected from the group consisting of methyl, ethyl, propyl, butyl, pentyl, and poly-ethylene glycols (PEGS).

Embodiment 10. The method of any one of embodiments 1 to 9, wherein the maleimide is N-ethyl-maleimide (NEM).

Embodiment 11. The method of any one of embodiments 1 to 10, wherein the heavy isotopologue of the maleimide is d5-NEM.

Embodiment 12. The method of any one of embodiments 1 to 11, wherein, for step d), the reducing agent is added in excess to residual maleimide.

Embodiment 13. The method of any one of embodiments 1 to 12, wherein, for step e), the heavy isotopologue of the maleimide is added in excess to the reducing agent previously added for step d).

Embodiment 14. The method of any one of embodiments 1 to 13, wherein the biological sample is a blood sample, such as a plasma sample, a serum sample or a whole-blood sample, or a tissue sample, preferably a biopsy sample, in particular a needle aspiration biopsy sample.

Embodiment 15. The method of any one of embodiments 1 to 14, wherein the biological sample comprises cells which comprise GSH and GSSG.

Embodiment 16. The method of embodiment 15, further comprising the step of lysing the cells.

Embodiment 17. The method of any one of embodiments 1 to 16, further comprising the step of adding a buffer solution to the biological sample before said contacting step b), preferably wherein the buffer solution contains the maleimide.

Embodiment 18. The method of embodiment 17, wherein the buffer solution has a pH between 6 and 8, preferably between 6.25 and 7.75, in particular between 6.5 and 7.5.

Embodiment 19. The method of embodiment 17 or 18, wherein the buffer solution is added directly to said blood sample, such as said plasma sample, said serum sample or said whole-blood sample, or said tissue sample, preferably wherein the tissue sample is a biopsy sample, in particular a needle aspiration biopsy sample.

Embodiment 20. The method of any one of embodiments 17 to 19, wherein the buffer solution is added directly to said cells which comprise GSH and GSSG.

Embodiment 21. The method of any one of embodiments 1 to 20, further comprising the step of concentrating and/or drying the sample, or a fraction thereof, comprising the maleimide-alkylated GSH and preferably the heavy isotopologue thereof.

Embodiment 22. The method of any one of embodiments 1 to 21, further comprising incubating the biological sample at a temperature of from 5° C. to 45° C., preferably from 10° C. to 40° C., more preferably from 15° C. to 35° C., especially from 20° C. to 30° C. for a period of time during said contacting step b) and/or e).

Embodiment 23. The method of any one of embodiments 1 to 22, further comprising incubating the biological sample at a pH between 6 and 8, preferably between 6.25 and 7.75, in particular between 6.5 and 7.5, for a period of time during said contacting step b) and/or e).

Embodiment 24. A stabilised biological sample containing maleimide-alkylated GSH and a heavy isotopologue thereof, obtainable by the method of any one of embodiments 1 to 23.

Embodiment 25. A biological sample or standard for mass spectrometry containing a maleimide-alkylated GSH of formula I and a maleimide-alkylated GSH of formula II

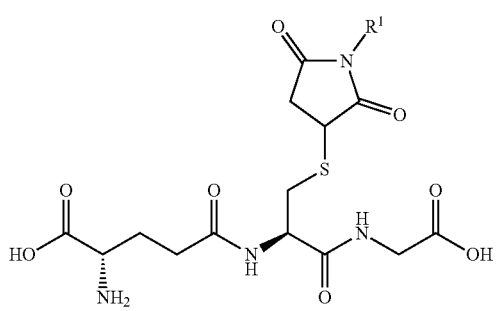

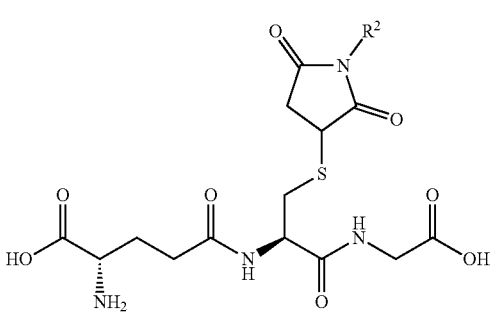

wherein $R^2$ is a heavy isotopologue of $R^1$, wherein $R^1$ is selected from the group consisting of methyl, ethyl, propyl, butyl, pentyl and PEGs.

Embodiment 26. The biological sample of embodiment 24 or 25, wherein the sample is dry.

Embodiment 27. The biological sample of any one of embodiments 24 to 26, wherein the maleimide-alkylated GSH and/or the heavy isotopologue thereof is present in the sample at a concentration of at least 0.0001 ppm, preferably at least 0.001 ppm, more preferably at least 0.01 ppm, even more preferably at least 0.1 ppm, in particular at least 1 ppm or even at least 10 ppm.

Embodiment 28. A method for quantifying maleimide-alkylated GSH and a heavy isotopologue thereof in a biological sample, the method comprising the following steps:

providing a biological sample as defined in any one of embodiments 24 to 27, optionally, purifying the biological sample in a liquid chromatography system, and analysing at least a fraction of the biological sample, which fraction contains at least a portion of the maleimide-alkylated GSH and the heavy isotopologue thereof, in a mass spectrometer to measure the abundance of the maleimide-alkylated GSH and the heavy isotopologue thereof.

Embodiment 29. A kit for stabilising a biological sample comprising GSH and GSSG for mass spectrometric analysis, the kit comprising
a first container containing a maleimide,
a second container containing a heavy isotopologue of the maleimide,
preferably a heavy isotopologue of a maleimide-alkylated

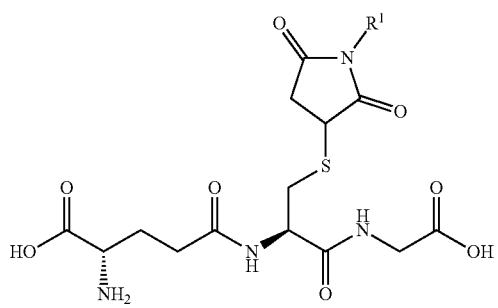

GSH of formula I
wherein $R^1$ is selected from the group consisting of methyl, ethyl, propyl, butyl, pentyl and PEGs, for use as an internal standard, preferably present in the first container or in a third container; and
preferably a fourth container containing a reducing agent, selected from the group consisting of phosphine-based reducing agents such as TCEP or tributylphosphine, and thiol-based reducing agents such as DTT, DTE or β-mercaptoethanol.

Embodiment 30. The kit of embodiment 29, wherein said first container is a blood collection tube; preferably wherein the kit comprises a plurality of said first container, in particular at least two, preferably at least five, even more preferably at least ten.

Embodiment 31. The kit of embodiment 30, wherein the blood collection tube is an evacuated blood collection tube.

Embodiment 32. The kit of embodiment 29 or 30, wherein the blood collection tube further comprises an anticoagulant preferably selected from the group consisting of heparin, ethylenediaminetetraacetate (EDTA), citrate and fluoride, preferably heparin or EDTA, or further comprising a coagulant preferably micronized silica particles or thrombin.

Embodiment 33. The kit of any one of embodiments 30 to 32, wherein the blood collection tube is a serum separator tube.

Embodiment 34. The kit of any one of embodiments 29 to 33, wherein the maleimide is present in its solid form in said first container.

Embodiment 35. The kit of any one of embodiments 29 to 34, wherein said heavy isotopologue of the maleimide-alkylated GSH is present in its solid form in said first container, preferably in a pre-set molar amount.

Embodiment 36. The kit of any one of embodiments 29 to 34, wherein said third container is present and contains said heavy isotopologue of the maleimide-alkylated GSH.

Embodiment 37. The kit of any one of embodiments 29 to 36,

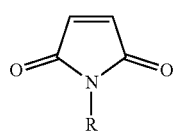

wherein the maleimide is:
wherein R is selected from the group consisting of methyl, ethyl, propyl, butyl, pentyl and PEGs.

Embodiment 38. The kit of any one of embodiments 29 to 37, wherein the maleimide is NEM.

Embodiment 39. The kit of any one of embodiments 29 to 38, wherein the heavy isotopologue of the maleimide is d5-NEM.

Embodiment 40. The kit of any one of embodiments 29 to 39, wherein the heavy isotopologue of the maleimide-alkylated GSH is 13C2, 15N-GSH-d5-NEM.

Embodiment 41. The kit of any one of embodiments 29 to 40, further comprising usage instructions.

Embodiment 42. A blood collection tube, containing a maleimide.

Embodiment 43. The blood collection tube of embodiment 42, wherein the maleimide is present in its solid form.

Embodiment 44. The blood collection tube of embodiment 42 or 43, wherein the blood collection tube is an evacuated blood collection tube.

Embodiment 45. The blood collection tube of any one of embodiments 42 to 44, wherein the maleimide is:

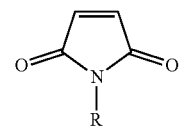

wherein R is selected from the group consisting of methyl, ethyl, propyl, butyl, pentyl and PEGs.

Embodiment 46. The blood collection tube of embodiment any one of embodiments 42 to 45, wherein the maleimide is NEM.

Embodiment 47. The blood collection tube of any one of embodiments 42 to 46, further comprising an anticoagulant preferably selected form the group consisting of heparin, ethylenediaminetetraacetate (EDTA), citrate and fluoride, preferably heparin or EDTA, or further comprising a coagulant preferably micronized silica particles or thrombin.

Embodiment 48. The blood collection tube of any one of embodiments 42 to 47, wherein the blood collection tube is a serum separator tube.

Embodiment 49. The blood collection tube of any one of embodiments 42 to 48, further comprising a heavy isotopologue of

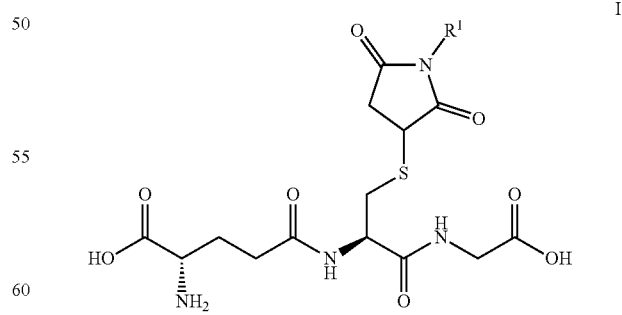

a maleimide-alkylated GSH of formula I
wherein $R^1$ is selected from the group consisting of methyl, ethyl, propyl, butyl, pentyl and PEGs; preferably wherein the heavy isotopologue is 13C2, 15N-GSH-d5-NEM.

Embodiment 50. The blood collection tube of embodiment 49, wherein the heavy isotopologue of the maleimide-alkylated GSH is present in its solid form.

Embodiment 51. The blood collection tube of embodiments 49 or 50, wherein the heavy isotopologue of the maleimide-alkylated GSH is present in the blood collection tube in a pre-set molar amount.

BRIEF DESCRIPTION OF THE DRAWINGS

The present invention is further illustrated by the following figures and examples, without being restricted thereto.

If not stated otherwise, error bars shown in the figures represent mean values±standard error of mean (SEM). For significance testing unpaired Student's t-test was performed with a p-value of 0.05 as significance threshold.

DETAILED DESCRIPTION

Examples

Example 1—Sample Preparation

Figure 1:
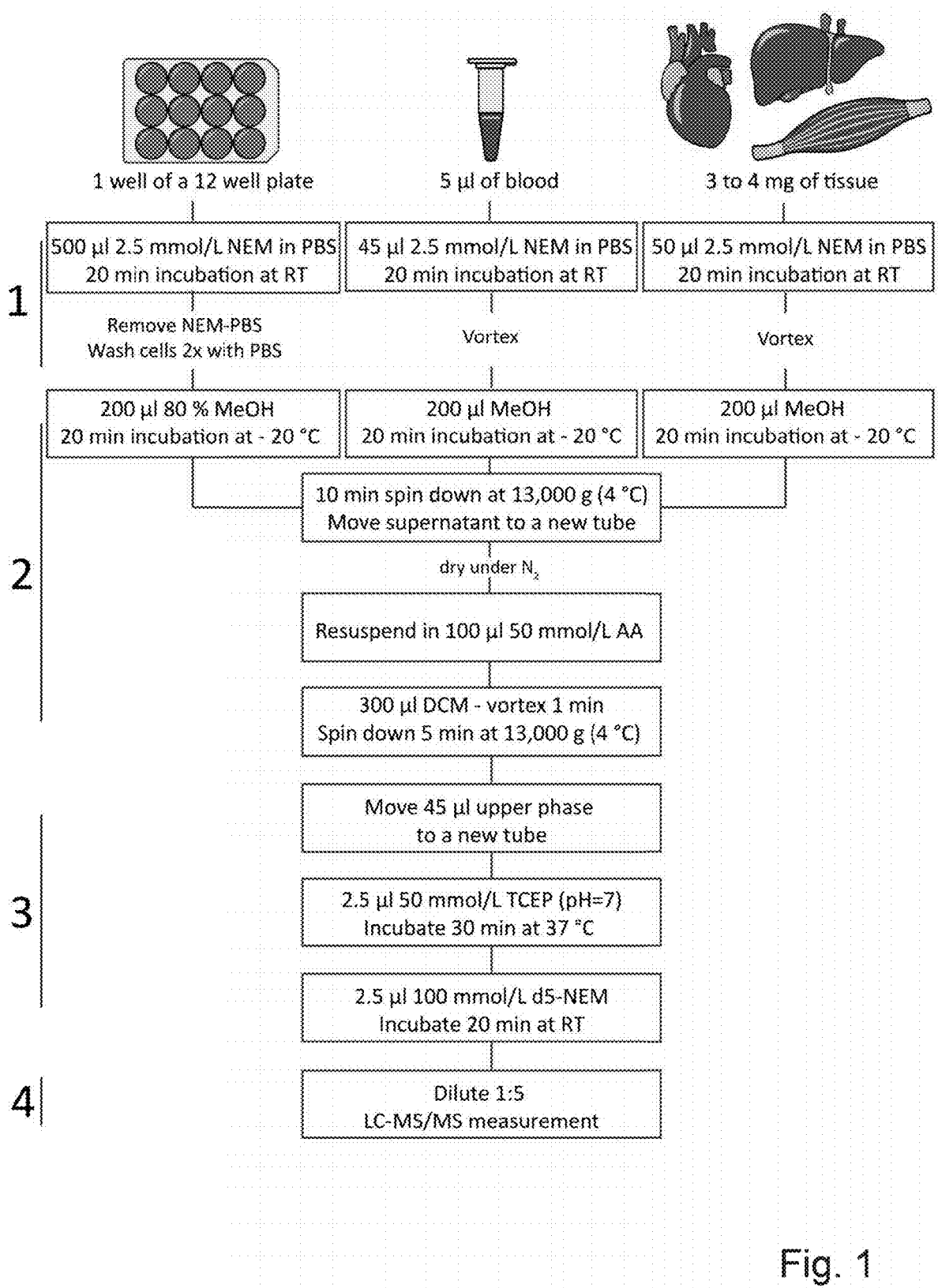
FIG. 1: Method workflow. In the first step (1) NEM was used to derivatize free GSH in a sample type specific manner. In the following step (2) proteins and excess NEM were removed by methanol precipitation and dichloromethane extraction. Next (3) GSSG in the samples was reduced to GSH which is then derivatized to GSH-d5-NEM. Finally, analytes are measured simultaneously by MRM-based LC-MS/MS (cf. Giustarini et al.).

Cell culture: A549 human lung carcinoma cells were obtained from CLS Cell Lines Service, Eppelheim, Germany, and were cultured in RPMI medium supplemented with 10% fetal bovine serum and 2 mmol/L glutamine in a 5% $CO_2$, 37° C. incubator. For $H_2O_2$ treatment, cells were seeded in 12-well plates (300000 cells/well) and after a day in culture treated with 500 µl of control ($Ca^{2+}$, $Mg^{2+}$-PBS) or 100 µmol/L $H_2O_2$ in $Ca^{2+}$, $Mg^{2+}$-PBS for 15 min followed by two PBS washing steps and the NEM (2.5 mmol/L) incubation step. The detailed stabilisation workflow is illustrated in FIG. 1 and example 2.

Blood samples: Blood samples were collected in VACUETTE® 3.5 ml tubes with Z Serum Separator Clot Activator 13×75 red cap-yellow ring, non-ridged (Greiner bio-one, Vienna, Austria). All blood collection tubes were customized prior to blood sampling in the following way: To each tube for direct NEMylation 100 µL of 87.5 mmol/L NEM in PBS was added to reach a final concentration of 2.5 mmol/L NEM after blood would fill the tube (NEM 0 min samples). To each tube of control samples (delayed NEM addition samples), 100 µL of PBS was added instead. For serum collection, all blood samples were coagulated for 30 min at room temperature (RT). After coagulation, samples were centrifuged at 1,300×g at RT for 20 min. All plasma samples were immediately centrifuged for 10 min at RT at 1,300×g. Whole blood samples were kept at 4° C. for 30 min. After these dedicated processing times and temperatures (50 min at RT for serum, 10 min at RT for plasma and 30 min at 4° C. for whole blood), 5 µl of each sample was pipetted out of the VACUETTE® tubes into 1.5 ml microcentrifuge tubes containing either 45 µl PBS (NEM 0 samples) or 45 µl of 2.5 mmol/L NEM in PBS (delayed NEM addition samples). The detailed stabilisation workflow is illustrated in FIG. 1 and example 2.

Tissue samples: For heart tissue lysis 4×10 s sonication steps at 70% amplitude were performed (Bandelin, Berlin, Germany). 4-7 mg of heart tissue was then processed according to the workflow shown in FIG. 1.

Example 2—Inventive Sample Stabilisation Method

Standards and reagents: Standards for GSH and GSSG were prepared as 10 mmol/L stock solutions in ultrapure water. For calibration curves, stock solutions were diluted in 50 mmol/L ammonium acetate buffer (AA, pH=7.0). NEM and d5-NEM were prepared as 100 mmol/L stock solutions in water. Tris(2-carboxyethyl)phosphine (TCEP) was used as 50 mmol/L stock solution prepared in 50 mmol/L AA buffered to pH=7.0. The stock solution of the internal standard (IS, $^{13}C_2$, $^{15}$N-GSH-d5-NEM) was prepared by reacting 2 mmol/L glutathione-(glycine-$^{13}C_2$, $^{15}$N) (Cambridge Isotope laboratories, Mass., USA) with 50 mmol/L d5-NEM in 50 mmol/L AA, with subsequent extraction of residual d5-NEM with dichloromethane. Final IS concentration was determined by analyzing a 1:100 dilution in 50 mmol/L AA by LC-MS/MS and matching signal intensity to the calibration curve of unlabeled GSH-NEM.

Method overview: The method was tested and fully optimized for three different sample types: cells, blood and tissue. In clinical measurements available sample amount is often a limiting factor. The high sensitivity of the presented method enables analysis of scarce samples as minimal sample amounts are required. Typically, 5 µL of blood, 3-5 mg of tissue sample or 300.000 cells were used as starting material. Therefore, the method is also suitable for samples acquired using minimally invasive techniques such as fine needle aspiration biopsies (FNAB)(~500.000 cells per FNAB). At the first step (FIG. 1, step 1) free glutathione was quenched with 2.5 mmol/L NEM solution for 20 min at room temperature (RT). Then cold 80% methanol (MeCH) was used to precipitate proteins from the sample (FIG. 1, step 2). At this step the internal standard (IS) can be introduced. Upon centrifugation the supernatant was transferred to a new reaction tube and dried under a stream of nitrogen. In order to maintain optimal pH dried samples were re-suspended in fl00 µl of 50 mmol/L AA and excess NEM was removed by extraction with dichloromethane. The aqueous phase was transferred to a new tube and subjected to reduction with TCEP followed by d5-NEM derivatization of GSSG derived GSH (FIG. 1, step 3). All three analytes GSH-NEM, GSH-d5-NEM and $^{13}C$, $^{15}$N-GSH-d5-NEM (IS) were then simultaneously measured by LC-MS/MS using an MRM-based approach (FIG. 1, step 4), see also example 4.

Example 3—Further Methodical Considerations

Figure 2:
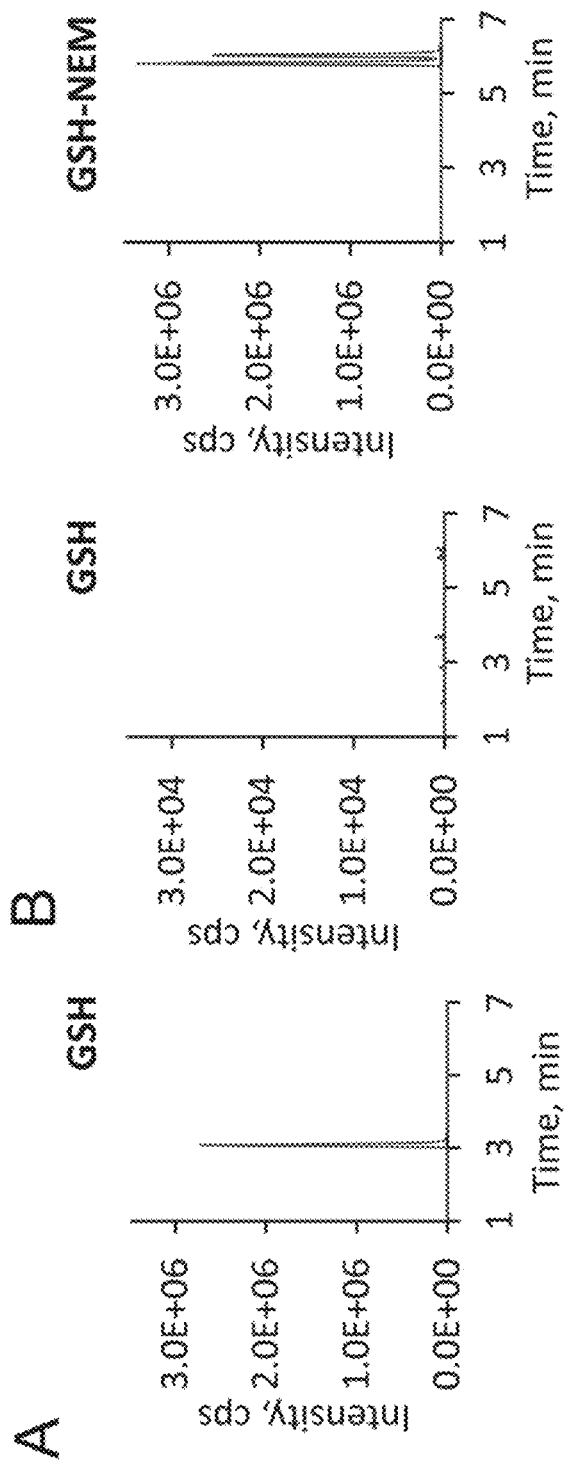
FIG. 2: Completeness of derivatization step. A standard solution of GSH (100 µmol/L) was completely derivatized at a NEM final concentration of 2.5 mmol/L after 20 min incubation at room temperature. A: GSH standard without the addition of NEM, B: Same GSH amount after incubation with 2.5 mmol/L NEM—no residual GSH was left and GSH was converted quantitatively to GSH-NEM. Note the factor 100 difference of the units in the scale of the y axis. Transitions of both GSH and GSH-NEM showed comparable signal responses as were also seen from the standard calibration curves. cps counts per second.
Figure 8:
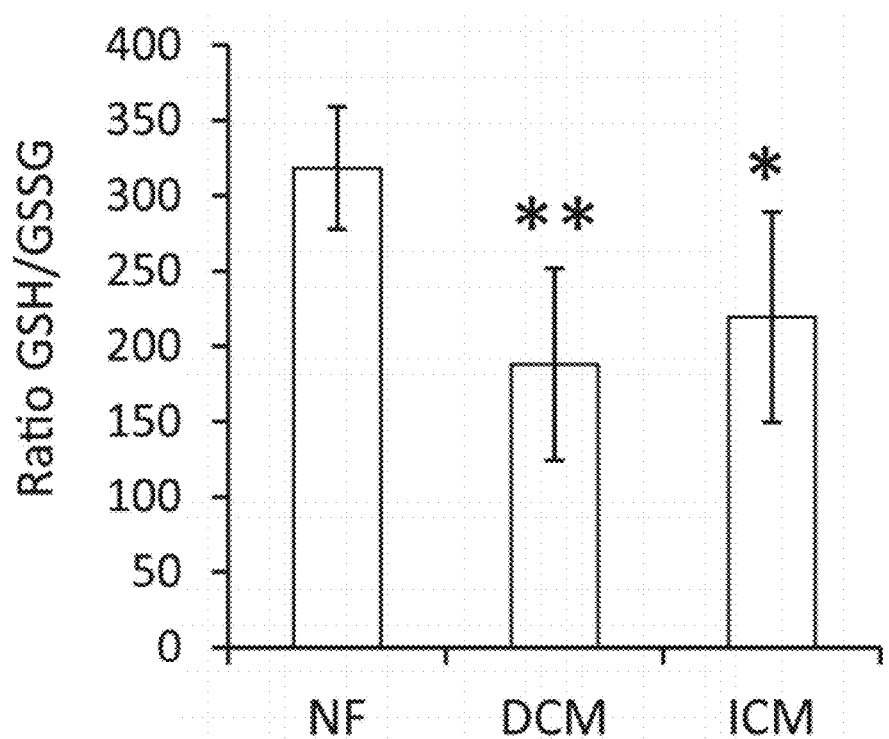
FIG. 8: ICM and DCM resulted in significant reduction of GSH/GSSG ratio as compared to non-failing heart tissue. Bar plot representing GSH/GSSG ratios±error propagated SEM (n=5 per group, Student's t-test, *p-value<0.05, **p-value<0.01), non-failing hearts (NF), dilative idiopathic cardiomyopathy (DCM), ischemic cardiomyopathy (ICM).

In preferred embodiments, NEM was added to the sample immediately after sampling. NEM turned out to be a particularly suitable derivatization reagent as it is cell permeable, reacts quickly and to completion (see FIG. 2 and FIG. 3A) and also inactivates GR (Giustarini et al., 2013). As a way to ensure complete derivatization of even more challenging samples such as tissue pieces, such samples were incubated for 20 min at room temperature. The latter results (FIG. 8) were obtained by simply vortexing 3-7 mg of cardiac muscle tissue cut into small pieces in NEM-containing PBS, without the need for additional lysis steps which greatly simplifies sample handling.

After GSH derivatization in cells or tissues, samples are preferably lysed to release polar metabolites and proteins, while lipids and other cell debris are preferably removed. This can either be achieved by acidic precipitation or by addition of polar organic solvents. As NEM alkylation is preferably performed at near neutral pH for high selectivity and reactivity, and one of the subsequent steps is labeling GSSG derived GSH with isotopically labeled NEM, the presented method employs 80% cold methanol for this purpose. The internal standard is ideally also spiked into this extraction solution to monitor extraction efficiency and analyte recovery of the following extraction steps. Precipitated proteins and cell debris were pelleted by centrifugation and the liquid phase was transferred to a new microcentrifuge tube. The solvent may be removed under a stream of nitrogen or by rotary evaporation.

Dried samples were then re-suspended in 50 mmol/L AA (pH=7.0). Here, pH control is important as at pH>7.5 NEM reacts also with amino groups, which could lead to over-alkylation of GSH at the free α-amino group of the γ-coupled glutamine.

Excess non-isotopically labeled NEM from the first alkylation step was then removed by a single dichloromethane liquid-liquid extraction step (sample: dichloromethane vol: vol 1:3). This single extraction resulted in removal of NEM beyond limit of detection (FIG. 3, B) and potential residual NEM was additionally quenched in the next step.

Figure 3:
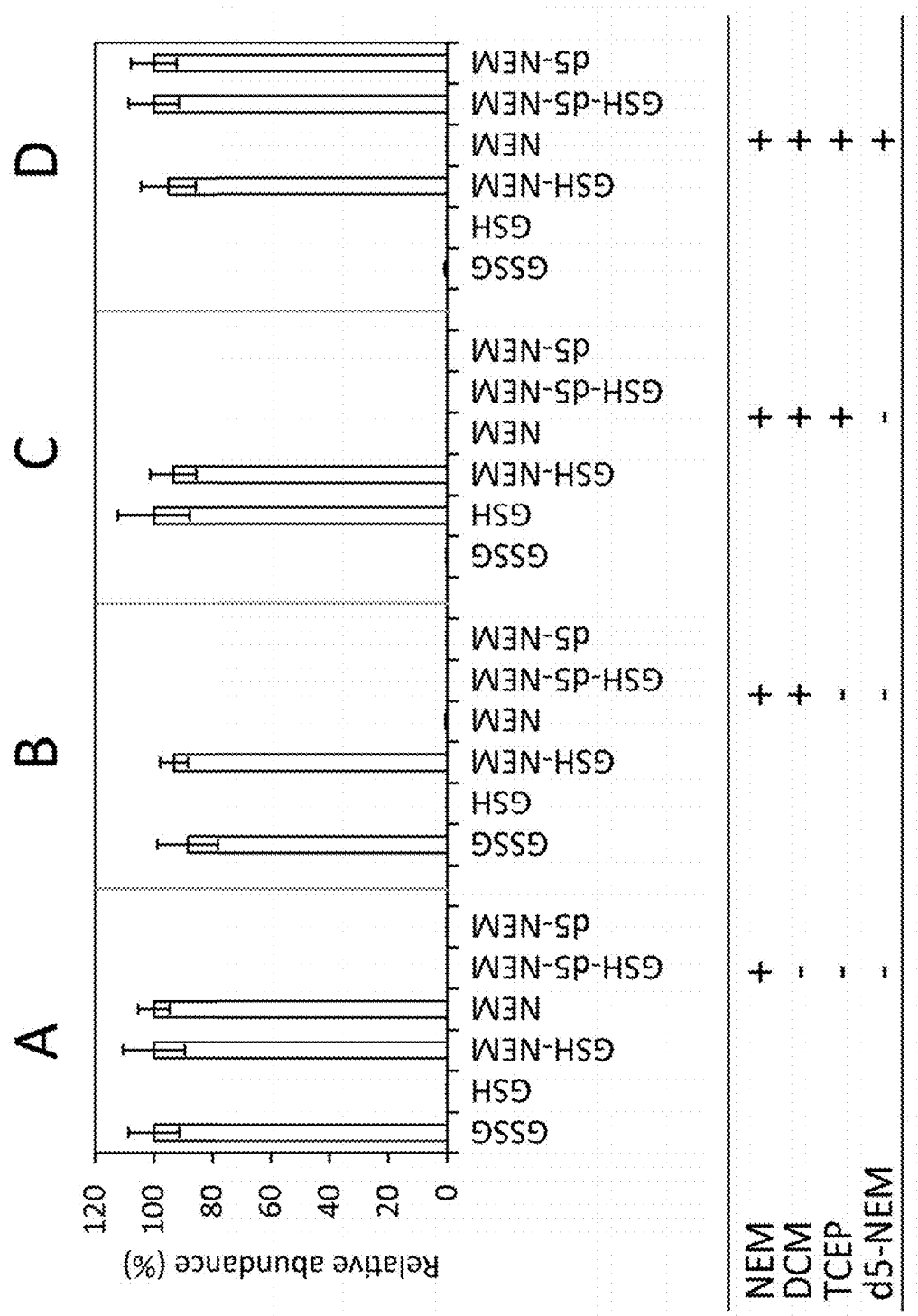
FIG. 3: Step by step completeness and selectivity of derivatization. Four technical replicates of 100 µmol/L of GSH and 10 µmol/L of GSSG standard were mixed and processed as indicated by plus icons in the table below the panel (steps A-D). At each step an equal aliquot of sample was used for measurement. Non-derivatized samples resulted in a massive standard deviation (S.D.) for both GSH and GSSG due to oxidation, thus they are not shown in this figure. Bars represent means of MRM signal areas normalized on the mean of MRM signal area of the corresponding analyte ±S.D. at its first appearance in the panel.

Initially, a quenching step to remove residual NEM with cysteine prior to reduction as described in literature (Danielson et al.) was tested. However, it surprisingly turned out that excess cysteine also partially reduced GSSG to GSH. It was therefore decided to simultaneously quench potentially residual NEM and reduce GSSG employing TCEP, which unexpectedly worked. TCEP (added to 2.5 mmol/L final concentration) therefore fulfilled a double role, scavenging residual non-isotopically labeled NEM and quantitatively reducing GSSG (FIG. 3, C). Because of the requirement of a controlled reaction pH, TCEP stock solution was adjusted to pH=7.0 with sodium hydroxide. To rule out labeling of GSSG derived GSH with non-isotopically labeled NEM, a control experiment using a mixture of GSH and GSSG standards in concentration ratio 10:1 (100 µmol/L GSH, 10 µmol/L GSSG) was performed, which is far below native ratios. Even under these extreme conditions of high GSSG favoring off-target labeling of GSSG derived GSH no significant contribution of GSSG derived GSH to the non-isotopically labeled GSH-NEM pools was observed (FIGS. 3, B and C). Finally, an excess of d5-NEM (5 mmol/L) was added to quantitatively label GSSG derived GSH (FIGS. 3, D).

Example 4—LC-MS/MS Method and Parameters

The following method was used in all MS experiments unless stated otherwise:

Chromatography was carried out on a Dionex UltiMate 3000 system equipped with a Zorbax SB-C18 column (50 mm×4.6 mm, 1.8 µm, Agilent, USA). The following gradient employing solvent A (0.1% formic acid in water) and solvent B (0.1% formic acid in acetonitrile) at a flow rate of 0.3 ml/min was applied: 0-10 min 1-30% B, 10-15 min 30-70% B, 15-20 min 1% B. Injection volume was 10 µl. The ABSciex 4000 QTRAP mass spectrometer used for detection was operated in positive MRM mode. A list of transitions with retention times and collision energies (CE) of analytes is shown in Table 1. Global instrument parameters: Curtain gas 20 (arbitrary units), collision gas high, ion spray voltage (IS) 4500 V, temperature 450° C., ion source gas 1 and 2: 25 (arbitrary units) and 40 (arbitrary units), declustering potential 50 V and entrance potential 10 V. As GSH-NEM is a diastereomer, all three GSH-NEM analytes (GSH-NEM, GSH-d5-NEM and $^{13}C_2$, $^{15}$N-GSH-d5-NEM) elute as twin peaks. The sum of areas under both peaks was used for integration and quantification.

TABLE 1

MRM transitions and parameters per analyte. For each compound transition 1 (marked in bold) was used for quantification (CE—collision energy, CXP—collision cell exit potential).

| Analyte name | Q1 Mass (amu) | Q3 Mass (amu) | Dwell time (ms) | CE (V) | CXP (V) |
|---|---|---|---|---|---|
| GSSG (Transition 1) | 613.2 | 355.3 | 35 | 33 | 14 |
| GSSG (Transition 2) | 613.2 | 484.2 | 35 | 25 | 12 |
| GSH (Transition 1) | 308 | 179 | 35 | 19 | 15 |
| GSH (Transition 2) | 308 | 76.23 | 35 | 47 | 15 |
| GSHNEM (Transition 1) | 433 | 201 | 35 | 35 | 15 |
| GSHNEM (Transition 2) | 433 | 84.2 | 35 | 59 | 15 |
| GSHd5NEM (Transition 1) | 438 | 206 | 35 | 35 | 15 |
| GSHd5NEM (Transition 2) | 438 | 84.2 | 35 | 59 | 15 |
| NEM (Transition 1) | 126 | 80 | 35 | 25 | 12 |
| NEM (Transition 2) | 126 | 98 | 35 | 19 | 16 |
| d5-NEM (Transition 1) | 131 | 80 | 35 | 25 | 12 |
| d5-NEM (Transition 2) | 131 | 98 | 35 | 19 | 16 |
| $^{13}C_2,^{15}N$ GSH-d5-NEM (IS) | 441 | 206 | 35 | 35 | 15 |

Example 5—Sensitivity of the Inventive Method

Figure 4:
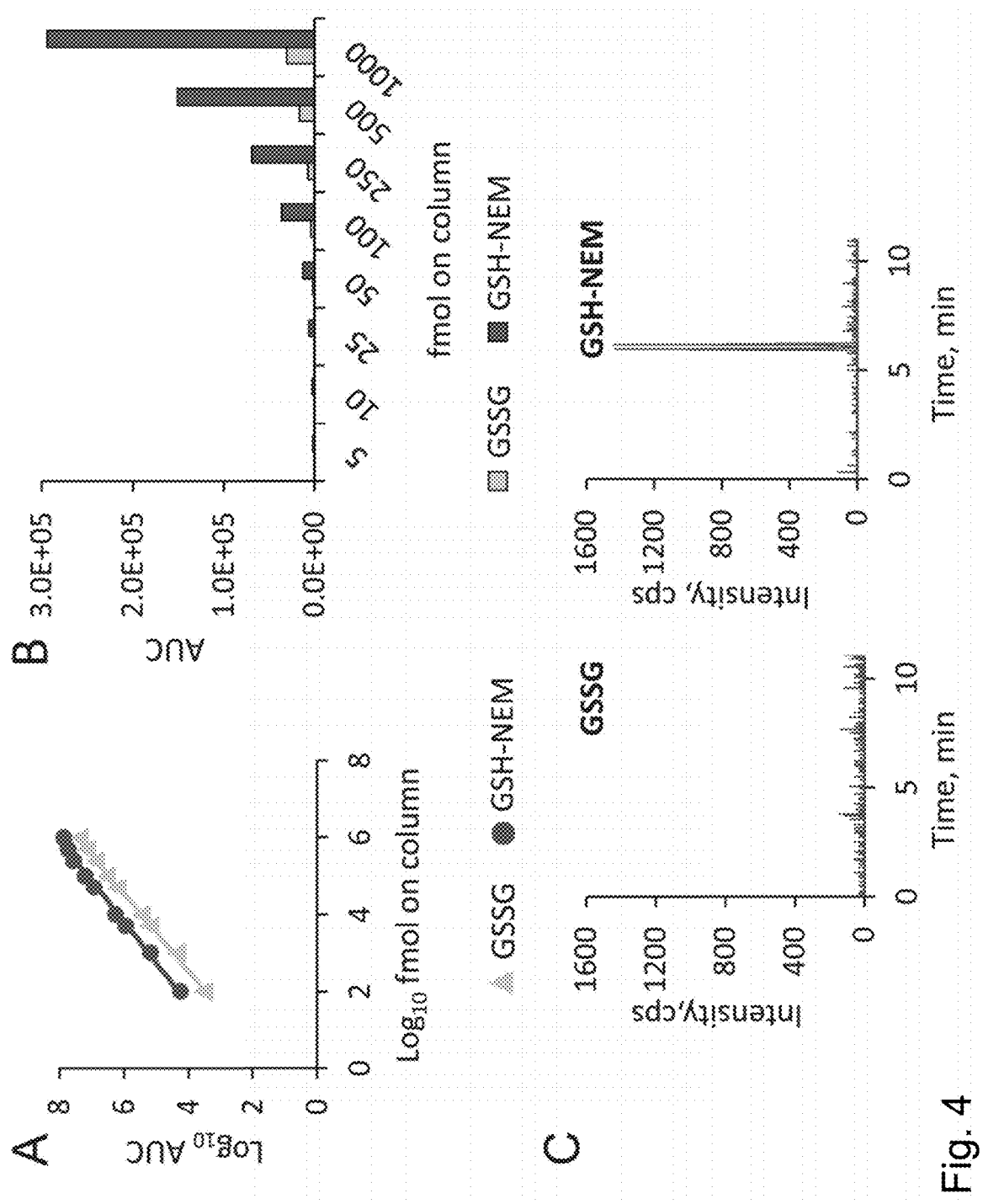
FIG. 4: GSH-NEM turned out to be a superior analyte over GSSG in terms of sensitivity. A: Calibration curves of GSH-NEM and GSSG. B: Comparison of signal area responses in low concentration range (5-1000 fmol on column) when GSSG was measured directly as GSSG as compared to being reduced, alkylated and measured as GSH-NEM. C: Example—25 fmol on column of GSSG was not directly detectable (left) but resulted in a readily quantifiable GSH-NEM peak (right).

The signal response of GSH-NEM was about five-fold higher than that of GSSG while noise levels were comparable throughout the whole dynamic range (FIG. 4, A). As GSSG reduction results in two molecules of GSH, overall sensitivity of the method for GSSG detection as GSH-d5-NEM was roughly 10-fold better than direct GSSG detection (see Table 2 below), which was entirely unexpected.

TABLE 2

Area under peak ratio of MRM signals of GSH-NEM to GSSG in the low concentration range. Reduction of GSSG with consequent d5-NEM derivatization of released GSH results in 9 to 10-fold higher sensitivity compared to direct measurement of GSSG.

| c (GSSG) [nmol/L] | MRM signal area ratio GSH-NEM/GSSG |
|---|---|
| 5 | 8.48 |
| 10 | 9.02 |
| 25 | 9.93 |
| 50 | 9.26 |
| 100 | 9.77 |
| Mean | 9.29 |

The boost in sensitivity was also reflected by the lower detection limits for GSSG. For example, 25 fmol of GSSG on column without previous reduction was below the limit of detection (LOD, monitored as MRM trace of GSSG, RT=3.71 min) while the same GSSG concentration which was reduced and alkylated with NEM resulted in a reliably quantifiable GSH-NEM peak with a signal to noise ratio (S/N) of more than 10 (MRM GSH-NEM) (FIG. 4, C). 10-fold greater sensitivity (presented for low concentration range in FIG. 4, B) yields a lower LOD and limit of quantification (LOQ) for GSH-NEM. LOD for GSSG was 50 fmol on column, while for GSSG measured as GSH-NEM that value was 5 fmol on column (with S/N ratios of 7.5 and 7, respectively). LOQ was 100 fmol on column for GSSG (S/N=11.5) and 10 fmol on column for GSSG measured as GSH-NEM (S/N=13), respectively.

Figure 5:
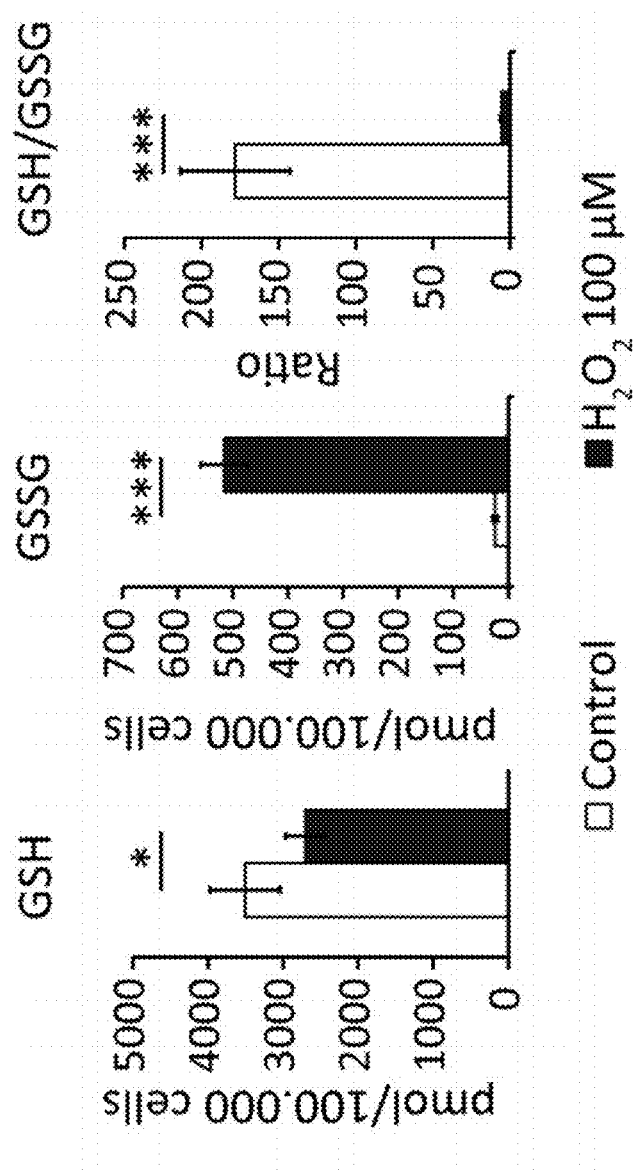
FIG. 5: Cellular oxidative stress reflected by reduced GSH/GSSG ratio. A549 cells treated with 100 µmol/L $H_2O_2$ for 15 min showed depletion of GSH and a rise in GSSG levels resulting in a vast reduction of the GSH/GSSG ratio (data from 2 independent experiments, n=6-8 replicates per condition, Student's t-test, *p-value<0.05, ***p-value<0.001).

Example 6—Applying the Inventive Sample Stabilisation Method to Cell Culture Samples The inventive approach was applied to cell culture samples (see example 1 for sample preparation). A single well of a 12-well cell culture plate (around 300.000 cells) proved to be sufficient for analysis. It should be noted that the sample could even be further diluted (A 1:5 dilution still provided high quality signals for all analytes). To functionally validate the procedure, oxidative stress was induced in A549 lung carcinoma cells by treatment with 100 µmol/L $H_2O_2$ for 15 min in two individual experiments. Incubation with $H_2O_2$ depleted intracellular GSH values yielding GSSG (measured as GSH d5 NEM) and hence a drastically reduced GSH/GSSG ratio (FIG. 5).

Example 7—Applying the Inventive Sample Stabilisation Method to Blood Samples

The inventive approach was applied to blood samples (see example 1 for sample preparation). The increased sensitivity of the inventive approach turned out to be particular beneficial when sample size is limited and/or if the sample has a very low GSSG concentration as in the case of blood samples where the GSH/GSSG ratio is 3-20 fold larger compared to solid tissues and cultured cells. Therefore, when blood GSH and GSSG levels are assessed even the slightest artificial oxidation of GSH during sample preparation can lead to overestimation of GSSG even as high as 7-50 fold. The most prominent GSSG artefact effect results from delayed NEM addition after blood collection leading to rapid depletion of GSH.

To illustrate this effect, we investigated how delayed NEM addition affects GSH and GSSG levels. Blood vacuum containers for full blood, plasma and serum where customized by adding either NEM or PBS (control tubes) prior to being employed for collecting blood from 5 healthy volunteers. EDTA plasma was centrifuged at room temperature immediately after collection for 10 min. Serum was allowed to clot at room temperature for 30 min in an upright position before being centrifuged for 20 min. NEM was added to both plasma and serum control tubes (which had been customized with PBS only) immediately after centrifugation. Whole blood samples were stored at 4° C. for 30 min prior to addition of NEM to the control tubes.

Figure 7:
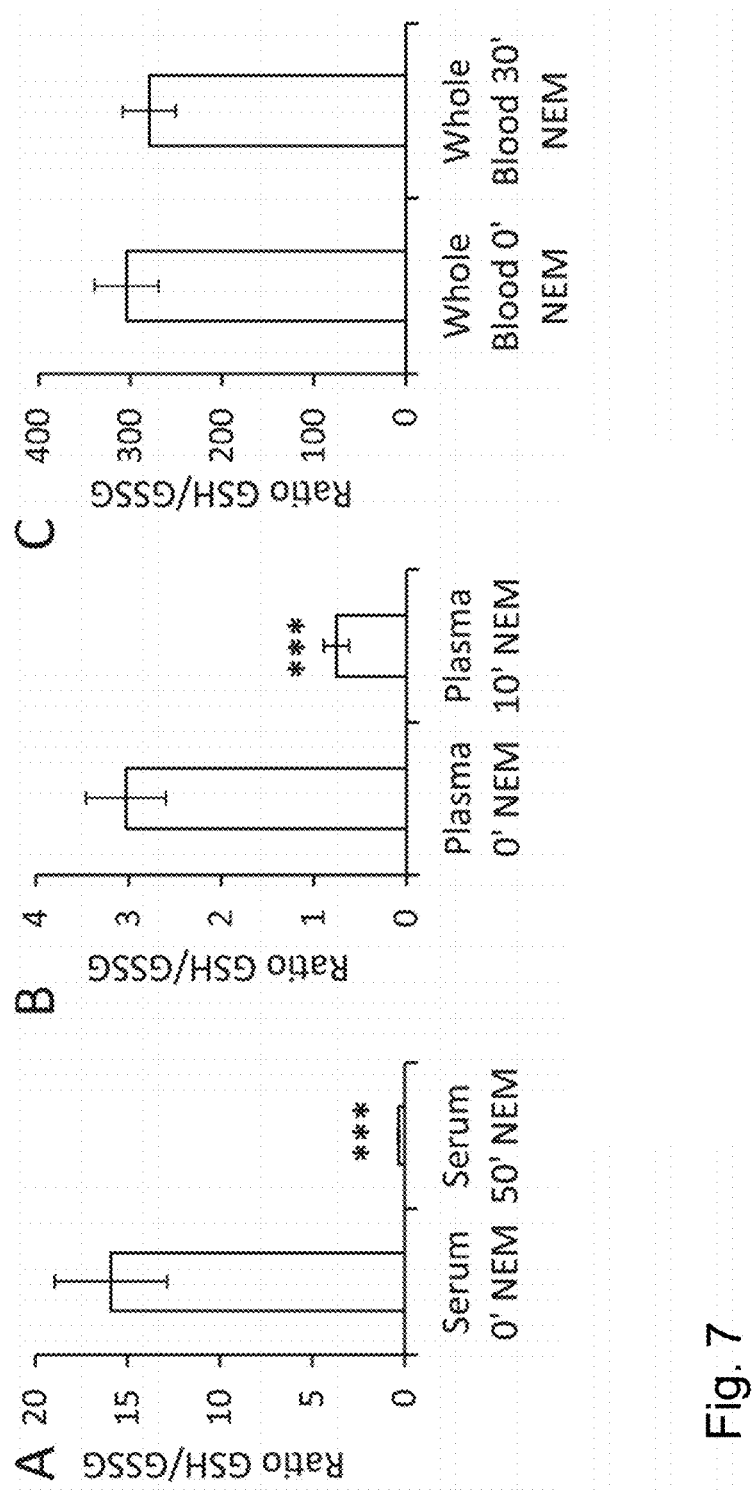
FIG. 7: Delay in NEM addition resulted in reduced GSH/GSSG ratios in serum and plasma samples. A: GSH/GSSG ratio is reduced in serum if NEM is added after preparation (50 min at RT) instead of immediately. B: Effect of plasma preparation time (10 min at RT) prior to NEM addition on GSH/GSSG ratio of plasma. C: 30 min incubation of whole blood at 4° C. did not alter the GSH/GSSG ratio. Bars represent mean ratio±error propagation calculated from S.E.M. (n=5, Student t-test, ***p-value<0.001).

Delays between sample collection and NEM addition resulted in reduction of measured GSH/GSSG ratios in serum and plasma but not in whole blood (FIG. 7). As serum preparation was the lengthiest procedure (50 min at RT) the effect was more pronounced (FIG. 7A) than for plasma (10 min at RT) (FIG. 7B). It should be noted that in serum and plasma absolute GSH concentrations represented only 0.1-3% of those measured in full blood.

Delayed addition of NEM is especially of concern when a strictly time controlled processing cannot be guaranteed as is often the case in a clinical setup. Immediate derivatization of GSH is therefore highly preferred for accurate determination of the redox state. In case instantaneous NEM addition is not possible whole blood samples can be kept refrigerated at 4° C. for up to 30 min without having an effect on the GSH/GSSG ratio (FIG. 7C).

Figure 6:
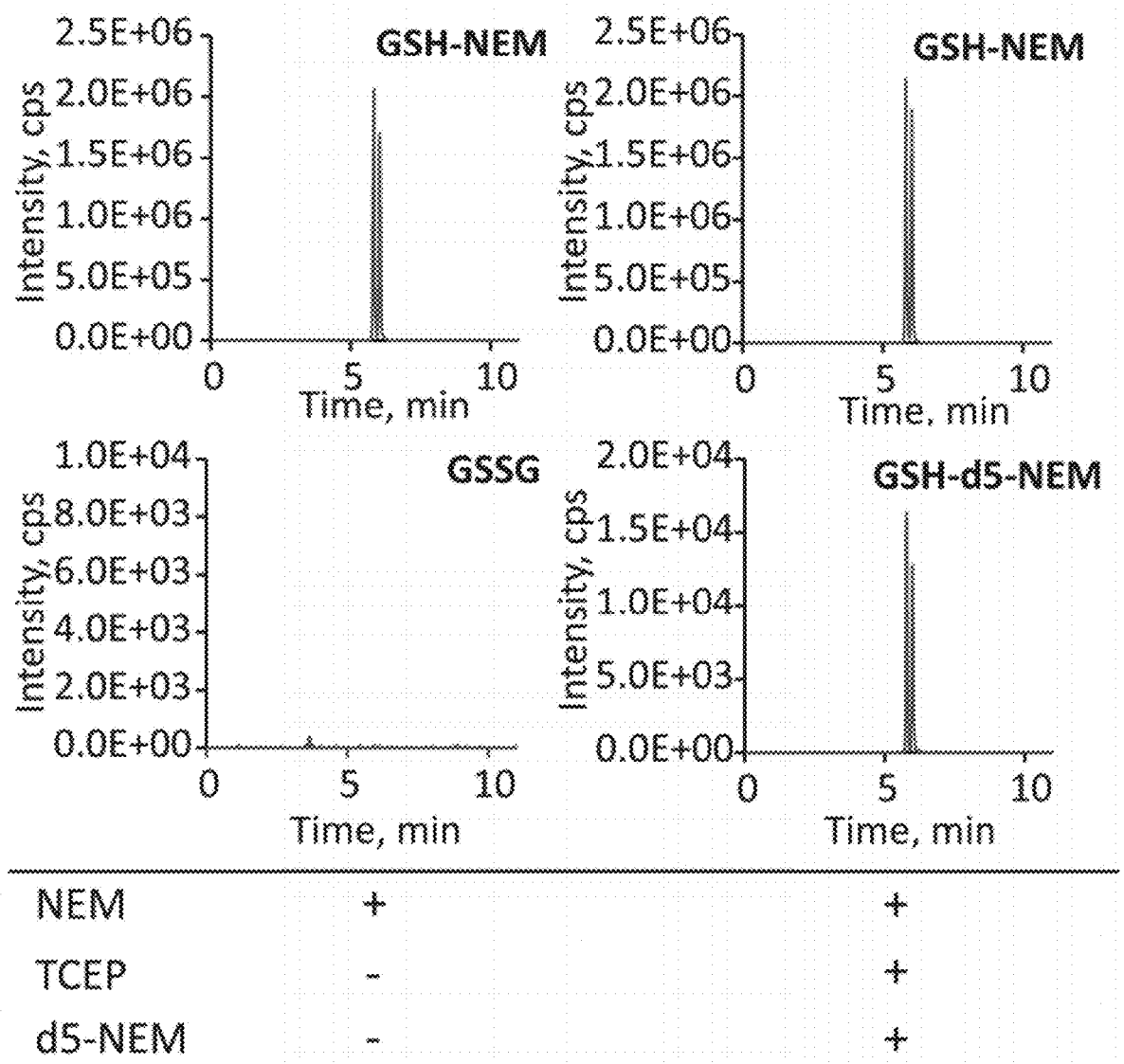
FIG. 6: Detection of GSSG in minimal amounts of whole blood. In 1 µl of whole blood no quantifiable GSSG peak was directly detectable (left), while reduction of GSSG with TCEP to GSH and alkylation with d5-NEM resulted in clearly detectable GSH-d5-NEM (right).

The improved sensitivity for GSSG quantification becomes apparent when analyzing GSSG from 1 µL of whole blood (FIG. 6). While direct measurement of GSSG did not yield a quantifiable MRM peak, reduction of GSSG with TCEP and subsequent alkylation with d5-NEM yielded prominent GSH d5 NEM peaks.

Example 8—Applying the Inventive Sample Stabilisation Method to Heart Tissue Samples To demonstrate its applicability on biopsy material, heart tissue samples (see example 1 for sample preparation) were subjected to the inventive method. Two patient groups suffering from dilated cardiomyopathies, idiopathic (DCM) and ischemic types (ICM) were compared to healthy controls. As little as 4-7 mg of flash-frozen heart tissue was used as starting material. Nevertheless, it was surprisingly possible to dilute the processed sample 1:5 for measurement and still reliably quantify both GSH and GSSG.

Samples from patients suffering from dilated cardiomyopathies showed significantly reduced GSH/GSSG ratios compared to healthy donors' non-failing heart tissue (NF) (FIG. 8) supporting that low GSH/GSSG ratio is a biomarker of the failing heart.

NON-PATENT REFERENCES

Apuy, Julius L., et al. "Ratiometric pulsed alkylation/mass spectrometry of the cysteine pairs in individual zinc fingers of MRE-binding transcription factor-1 (MTF-1) as a probe of zinc chelate stability." Biochemistry 40.50 (2001): 15164-15175.

Danielson S R, Held J M, Oo M, Riley R, Gibson B W, Andersen J K. Quantitative mapping of reversible mitochondrial Complex I cysteine oxidation in a Parkinson disease mouse model. J Biol Chem. 2011; 286(9):7601-8.

Deponte M. Glutathione catalysis and the reaction mechanisms of glutathione-dependent enzymes. Biochim Biophys Acta. 2013; 1830(5):3217-66.

Forman H J, Zhang H, Rinna A. Glutathione: overview of its protective roles, measurement, and biosynthesis. Mol Aspects Med. 2009; 30(1-2):1-12.

Giustarini D, Dalle-Donne I, Milzani A, Fanti P, Rossi R. Analysis of GSH and GSSG after derivatization with N-ethylmaleimide. Nat Protoc. 2013; 8(9):1660-9.

Giustarini D, Tsikas D, Colombo G, Milzani A, Dalle-Donne I, Fanti P, et al. Pitfalls in the analysis of the physiological antioxidant glutathione (GSH) and its disulfide (GSSG) in biological samples: An elephant in the room. J Chromatogr B Analyt Technol Biomed Life Sci. 2016; 1019: 21-8.

Griffith O W. Determination of glutathione and glutathione disulfide using glutathione reductase and 2-vinylpyridine. Anal Biochem. 1980; 106(1):207-12.

Jubiz, W., & Nolan, G. (1978). N-Ethylmaleimide prevents destruction of corticotropin (ACTH) in plasma. Clinical chemistry, 24(5), 826-827.

Keith M, Geranmayegan A, Sole M J, Kurian R, Robinson A, Omran A S, et al. Increased oxidative stress in patients with congestive heart failure. J Am Coll Cardiol. 1998; 31(6):1352-6.

Leonard, Stephen E., and Kate S. Carroll. "Chemical 'omics' approaches for understanding protein cysteine oxidation in biology." Current opinion in chemical biology 15.1 (2011): 88-102.

Lu S C. Glutathione synthesis. Biochim Biophys Acta. 2013; 1830(5):3143-53.

McDonagh, B., Sakellariou, G. K., Smith, N. T., Brownridge, P., & Jackson, M. J. (2014). Differential cysteine labeling and global label-free proteomics reveals an altered metabolic state in skeletal muscle aging. Journal of proteome research, 13(11), 5008-5021.

Mehra, Simmi, et al. "Stability of eosin-5'-maleimide dye used in flow cytometric analysis for red cell membrane disorders." Blood research 50.2 (2015): 109-112.

Moore, Tereza, et al. "A new LC-MS/MS method for the clinical determination of reduced and oxidized glutathione from whole blood." Journal of Chromatography B 929 (2013): 51-55.

Rajer M, Kmet M. Quantitative analysis of fine needle aspiration biopsy samples. Radiology and Oncology. 2005; 39(4):269-72.

Reinbold J, Koehler P, Rychlik M. Quantitation of glutathione and its oxidation products in erythrocytes by multiple-label stable-isotope dilution. Anal Biochem. 2014; 445:41-8.

Sentellas S, Morales-Ibanez O, Zanuy M, Alberti J J. GSSG/GSH ratios in cryopreserved rat and human hepatocytes as a biomarker for drug induced oxidative stress. Toxicol In Vitro. 2014; 28(5):1006-15.

Sinha, V., Wijewickrama, G. T., Chandrasena, R. E. P., Xu, H., Edirisinghe, P. D., Schiefer, I. T., & Thatcher, G. R. (2010). Proteomic and mass spectroscopic quantitation of protein S-nitrosation differentiates NO-donors. ACS chemical biology, 5(7), 667-680.

Sutton T R, Minnion M, Barbarino F, Koster G, Fernandez B O, Cumpstey A F, et al. A robust and versatile mass spectrometry platform for comprehensive assessment of the thiol redox metabolome. Redox biology. 2018; 16:359-80.

Svardal, Asbjorn M., Mohammad A. Mansoor, and Per M. Ueland. "Determination of reduced, oxidized, and protein-bound glutathione in human plasma with precolumn derivatization with monobromobimane and liquid chromatography." Analytical Biochemistry 184.2 (1990): 338-346.

Tietze F. Enzymic method for quantitative determination of nanogram amounts of total and oxidized glutathione: applications to mammalian blood and other tissues. Anal Biochem. 1969; 27(3):502-22.

Townsend D M, Tew K D, Tapiero H. The importance of glutathione in human disease. Biomedicine & Pharmacotherapy. 2003; 57(3-4):145-55.

Zitka O, Skalickova S, Gumulec J, Masarik M, Adam V, Hubalek J, et al. Redox status expressed as GSH:GSSG ratio as a marker for oxidative stress in paediatric tumour patients. Oncol Lett. 2012; 4(6):1247-53.

The invention claimed is:

1. A method of stabilising a biological sample comprising glutathione (GSH) and glutathione disulfide (GSSG), the method comprising the following steps:

a) providing the biological sample comprising GSH and GSSG;

b) contacting GSH and GSSG of the biological sample with a maleimide under conditions which allow alkylation of the sulfhydryl group of GSH with the maleimide to obtain maleimide-alkylated GSH, wherein the maleimide is N-ethyl maleimide (NEM);

c) separating excess maleimide from maleimide-alkylated GSH and GSSG by solvent extraction, wherein the solvent is an inorganic solvent selected from the group consisting of dichloromethane, chloroform, ethyl acetate, hexane, diethyl ether, and mixtures thereof;

d) contacting maleimide-alkylated GSH and GSSG after step c) with a reducing agent selected from the group consisting of tris(2-carboxyethyl) phosphine (TCEP), tributylphosphine, dithiothreitol (DTT), dithioerythritol (DTE) and β-mercaptoethanol, under conditions which allow reduction of GSSG by the reducing agent to obtain further GSH; and e) contacting maleimide-alkylated GSH and GSH after step d) with a heavy isotopologue of the maleimide under conditions which allow alkylation of the sulfhydryl group of GSH with the heavy isotopologue of the maleimide to obtain a heavy isotopologue of the maleimide-alkylated GSH;

whereby a stabilised biological sample, comprising the maleimide-alkylated GSH and the heavy isotopologue of the maleimide-alkylated GSH, is obtained;

wherein the heavy isotopologue of the maleimide is N-ethyl-D5-maleimide (D5-NEM).

2. The method of claim 1, wherein the biological sample is a blood sample, wherein step b) occurs in a blood collection tube pre-filled with the maleimide.

3. The method of claim 2, wherein the blood collection tube is further pre-filled with another heavy isotopologue of the maleimide-alkylated GSH for use as an internal standard.

4. The method of claim 1, wherein the reducing agent is TCEP.

5. The method of claim 1, wherein the biological sample further comprises protein and the method further comprising separating protein from maleimide-alkylated GSH and GSSG by solvent precipitation of the protein wherein the solvent is ethanol, methanol, acetonitrile or a mixture thereof; and wherein the separating is conducted before step c).

6. The method of claim 1, further comprising a step of concentrating and/or drying the sample after step e), comprising the maleimide-alkylated GSH and the heavy isotopologue of the maleimide-alkylated GSH.

* * * * *